United States Patent
Yoshikawa et al.

(10) Patent No.: US 12,324,651 B2
(45) Date of Patent: Jun. 10, 2025

(54) ACOUSTIC-WAVE MEASURING DEVICE, MATCHING-MATERIAL BAG, MATCHING GEL, SEPARATION FILM, AND ACOUSTIC-WAVE MEASUREMENT METHOD

(71) Applicant: Luxonus Inc., Kawasaki (JP)

(72) Inventors: Aya Yoshikawa, Kawasaki (JP); Takayuki Yagi, Kawasaki (JP); Yoshikiyo Yui, Kawasaki (JP); Yasufumi Asao, Kawasaki (JP); Takaaki Nakabayashi, Kawasaki (JP)

(73) Assignee: LUXONUS INC., Kawasaki (JP)

( * ) Notice: Subject to any disclaimer, the term of this patent is extended or adjusted under 35 U.S.C. 154(b) by 179 days.

(21) Appl. No.: 17/921,022

(22) PCT Filed: Apr. 22, 2021

(86) PCT No.: PCT/JP2021/016343
§ 371 (c)(1),
(2) Date: Oct. 24, 2022

(87) PCT Pub. No.: WO2021/215510
PCT Pub. Date: Oct. 28, 2021

(65) Prior Publication Data
US 2023/0127501 A1    Apr. 27, 2023

(30) Foreign Application Priority Data
Apr. 24, 2020 (JP) ................... 2020-077580

(51) Int. Cl.
*A61B 8/00* (2006.01)
*A61B 5/00* (2006.01)

(52) U.S. Cl.
CPC .......... *A61B 5/0095* (2013.01); *A61B 8/4281* (2013.01)

(58) Field of Classification Search
CPC .......... A61B 8/40; A61B 8/406; A61B 8/4272; A61B 8/4281
See application file for complete search history.

(56) References Cited

U.S. PATENT DOCUMENTS 6,128,523 A * 10/2000 Bechtold ................ A61B 5/055
601/4
2015/0320321 A1   11/2015 Oyama
(Continued)

FOREIGN PATENT DOCUMENTS

JP       2015-213533 A      12/2015
JP       2017-077410 A       4/2017
(Continued)

OTHER PUBLICATIONS

Machine translation of Nishimura (JP 2018079009, May 24, 2018).*
Jun. 8, 2021 International Search Report issued in Patent Application No. PCT/JP2021/016343.

*Primary Examiner* — Carolyn A Pehlke
(74) *Attorney, Agent, or Firm* — Oliff PLC

(57) ABSTRACT

An acoustic-wave measuring device includes: a support table having a support surface configured to support an examination subject, and an opening portion provided in the support surface to measure a predetermined examination site of the examination subject; a container located vertically below the support surface and capable of containing an acoustic matching material in a liquid or gel form; and a receiving element located vertically below the support surface and configured to receive an acoustic wave generated from the examination site, wherein a matching-material bag containing an acoustic matching material in a liquid or gel form or a matching gel having limited flowability and an acoustic control effect, and a placement unit for placement of the matching-material bag or the matching gel thereon are (Continued)

installable between the acoustic matching material contained in the container and the examination site.

16 Claims, 16 Drawing Sheets

(56) References Cited

U.S. PATENT DOCUMENTS

| | | | | |
|---|---|---|---|---|
| 2018/0100832 A1* | 4/2018 | Ebisawa | ............... | A61B 8/4494 |
| 2018/0271480 A1* | 9/2018 | Kawabata | ............. | A61B 8/4494 |
| 2018/0292358 A1* | 10/2018 | Ito | ......................... | A61B 8/0875 |
| 2019/0290939 A1* | 9/2019 | Watson | .................. | A61B 90/37 |
| 2019/0320907 A1 | 10/2019 | Nagae | | |
| 2021/0022705 A1* | 1/2021 | Suzuki | ..................... | A61B 8/15 |

FOREIGN PATENT DOCUMENTS

| | | |
|---|---|---|
| JP | 2018-079009 A | 5/2018 |
| JP | 2019-187617 A | 10/2019 |
| JP | 2019-195583 A | 11/2019 |

* cited by examiner

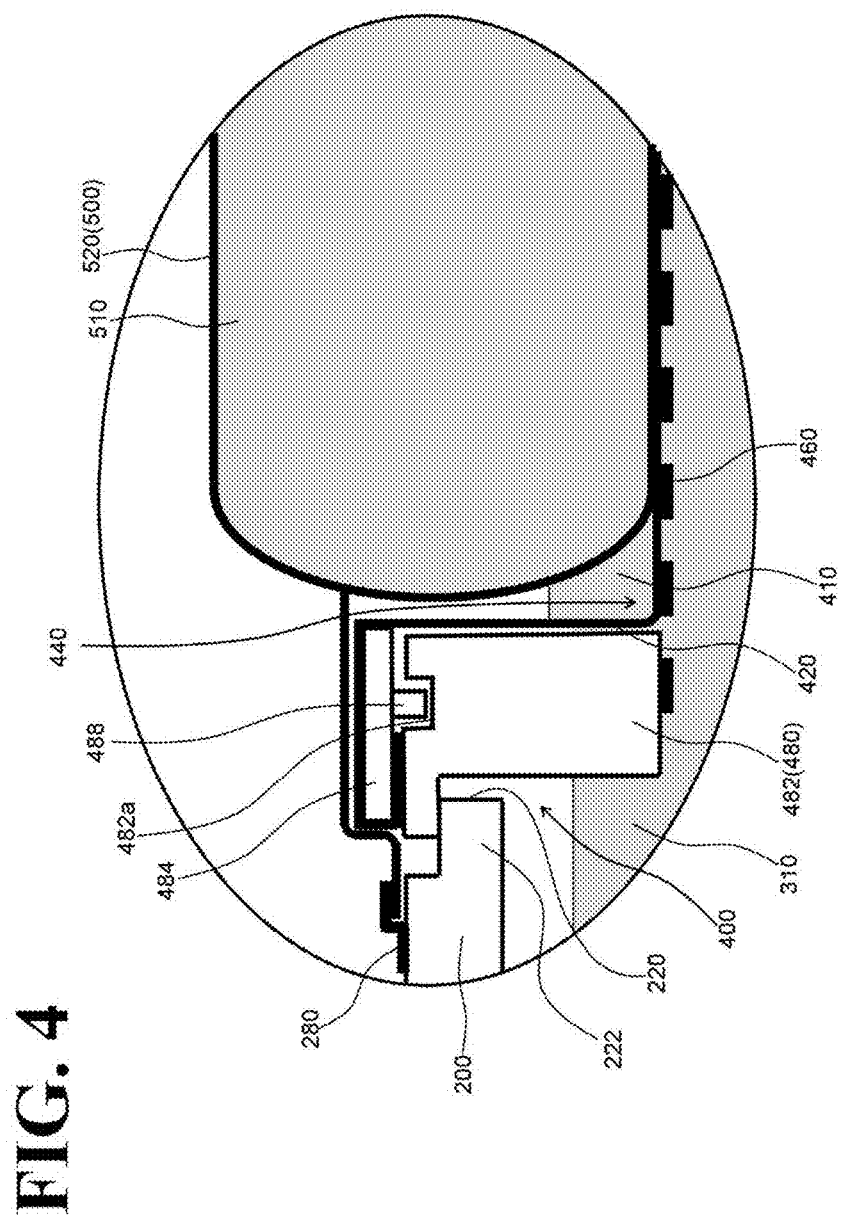

ACOUSTIC-WAVE MEASURING DEVICE, MATCHING-MATERIAL BAG, MATCHING GEL, SEPARATION FILM, AND ACOUSTIC-WAVE MEASUREMENT METHOD

TECHNICAL FIELD

The present invention relates to an acoustic-wave measuring device, a matching-material bag, a matching gel, a separation film, and an acoustic-wave measurement method.

BACKGROUND ART

In recent years, devices for measuring acoustic waves generated from an examination subject and obtaining characteristics information regarding the inside of the examination subject have been developed in the medical field, for example (e.g., Patent Document 1).

CITATION LIST

Patent Documents

JP 2018-079009A

SUMMARY OF INVENTION

Technical Problem

An object of the present invention is to achieve both reducing the burden on an examination subject and easily ensuring a clean state while ensuring appropriate acoustic matching.

Solution to Problem

According to an aspect of the present invention, an acoustic-wave measuring device is provided that includes:
a support table having a support surface configured to support an examination subject, and an opening portion provided in the support surface in order to measure a predetermined examination site of the examination subject;
a container located vertically below the support surface and capable of containing an acoustic matching material in a liquid or gel form; and
a receiving element located vertically below the support surface and configured to receive an acoustic wave generated from the examination site,
wherein a matching-material bag containing an acoustic matching material in a liquid or gel form, or a matching gel having limited flowability and an acoustic control effect, and a placement unit for placement of the matching-material bag or the matching gel thereon are installable between the acoustic matching material contained in the container and the examination site.

According to another aspect of the present invention, a matching material bag for use in the above-described acoustic-wave measuring device is provided.

According to yet another aspect of the present invention, a matching gel for use in the above-described acoustic-wave measuring device is provided.

According to yet another aspect of the present invention, a separation film for use in the above-described acoustic-wave measuring device is provided.

According to yet another aspect of the present invention, an acoustic wave measurement method is provided that includes:
preparing an acoustic-wave measuring device including a support table having a support surface and an opening portion provided in the support surface in order to measure a predetermined examination site of an examination subject, a container located vertically below the support surface and containing an acoustic matching material in a liquid or gel form, and a receiving element located vertically below the support surface;
placing the examination subject on the support surface of the support table; and
receiving an acoustic wave generated from the examination site, with use of the receiving element,
wherein in the preparing of the acoustic-wave measuring device,
a matching-material bag containing an acoustic matching material in a liquid or gel form, or a matching gel having limited flowability and an acoustic control effect, and a placement unit for placement of the matching-material bag or the matching gel thereon are installed between the acoustic matching material contained in the container and the examination site.

Effects of the Invention

According to the present invention, it is possible to achieve both reducing the burden on an examination subject and easily ensuring a clean state while ensuring appropriate acoustic matching.

BRIEF DESCRIPTION OF DRAWINGS

FIG. 4 is a schematic enlarged view of a part of an acoustic-wave measuring device according to a variation 1-1 of the first embodiment of the present invention.

DESCRIPTION OF EMBODIMENTS

Figure 1:
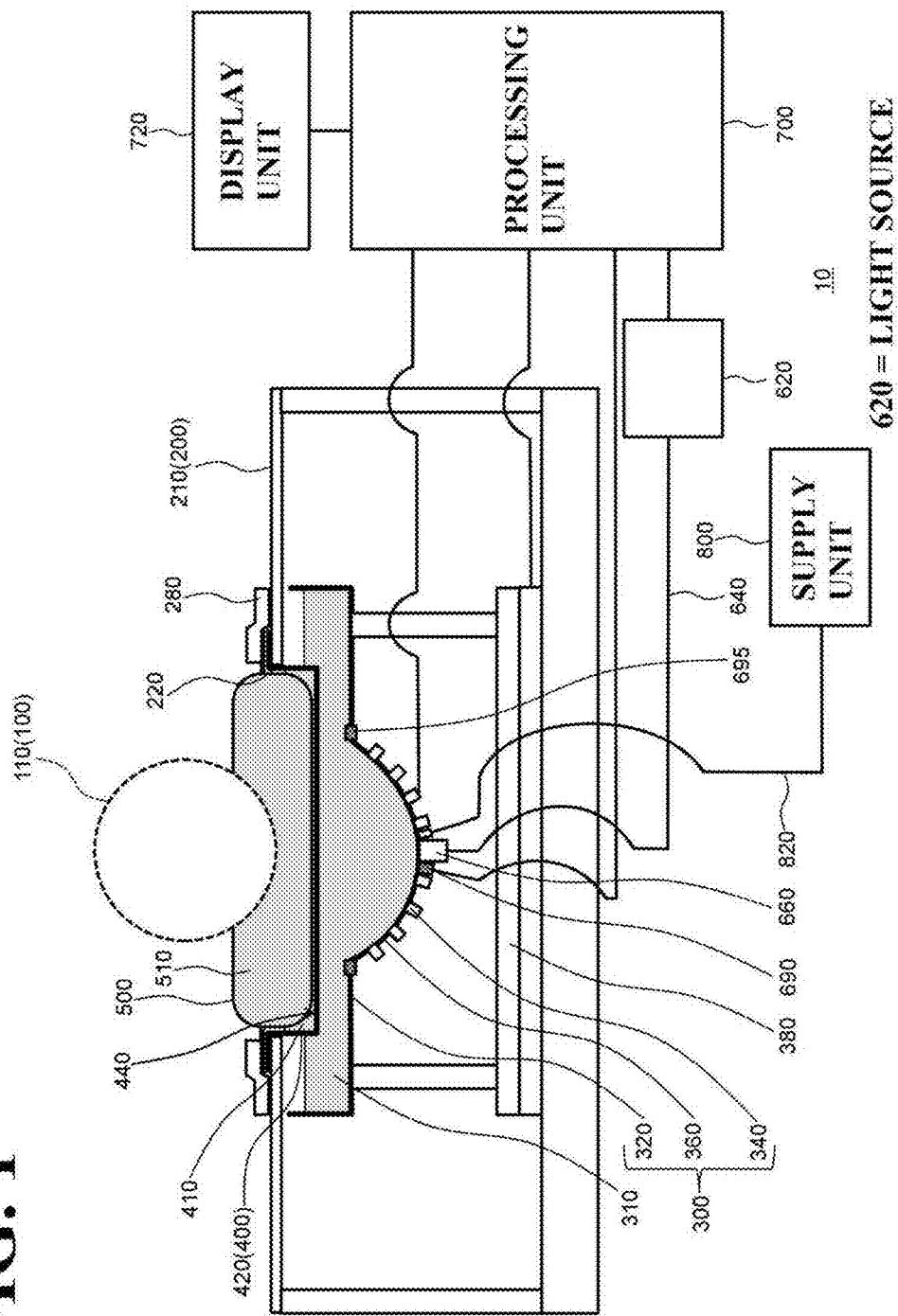
FIG. 1 is a schematic diagram showing an acoustic-wave measuring device according to a first embodiment of the present invention.

Findings Made by Inventors Etc.

First, the findings made by the inventors etc. will be described.

A conventional acoustic-wave measuring device (acoustic-wave receiving device) has, for example, a support table, a holding member, a liquid tank, and a transducer, as in the aforementioned Patent Document 1. The support table has a support surface for supporting an examination subject. The holding member stores a matching liquid for the examination subject side while holding a predetermined examination site of the examination subject. The liquid tank stores a transducer-side matching liquid under the support surface of the support table. The transducer is provided in the liquid tank and receives acoustic waves from the predetermined examination site of the examination subject via the matching liquid for the examination subject side, the holding member, and the transducer-side matching material.

Thus, as a configuration related to acoustic matching, the conventional acoustic-wave measuring device adopts a separated structure of "examination subject/matching liquid for the examination subject side/holding member/transducer-side matching liquid/transducer". This structure does not allow air to be present between the examination site and the transducer, thereby suppressing a decrease in acoustic wave measurement accuracy.

However, in the conventional acoustic-wave measuring device, the predetermined examination site of the examination subject is directly immersed in the matching liquid for the examination subject side. Since it is necessary to adopt a liquid tank having a depth that allows the matching liquid for the examination subject side to be contained, there is a possibility that when the examination site is inserted into the liquid tank, a part of the examination subject comes into contact with a corner of the liquid tank, or the examination subject is forced to be in a difficult position. This increases the burden on the examination subject. Moreover, the examination site becomes wet with the matching liquid for the examination subject side, which increases the burden on the examination subject and possibly gives a person who is the examination subject an unpleasant feeling. In addition, there are cases where examination clothes, a screen covering the examination site, or the like also become wet, thus degrading the measurement environment and further increasing the burden on the examination subject.

A separation film, which is installed to suppress cross-infection between examination subjects via the transducer-side matching liquid, is discarded before another examination subject is measured. Therefore, at least the matching liquid for the examination subject side needs to be removed before the separation film is discarded. At this time, with the conventional acoustic-wave measuring device, the matching liquid for the examination subject side stored in the holding portion is removed by absorbing the matching liquid using a sponge or the like, for example. Therefore, removing the matching liquid for the examination subject side is difficult and requires a long time.

Thus, it is difficult for the conventional acoustic-wave measuring device to achieve both reducing the burden on the examination subject and easily ensuring a clean state.

The present invention is based on the above findings made by the inventors etc.

First Embodiment of the Present Invention

The first embodiment of the present invention will be described below with reference to the drawings.

(1) Acoustic-Wave Measuring Device (Acoustic-Wave Receiving Device)

Figure 2:
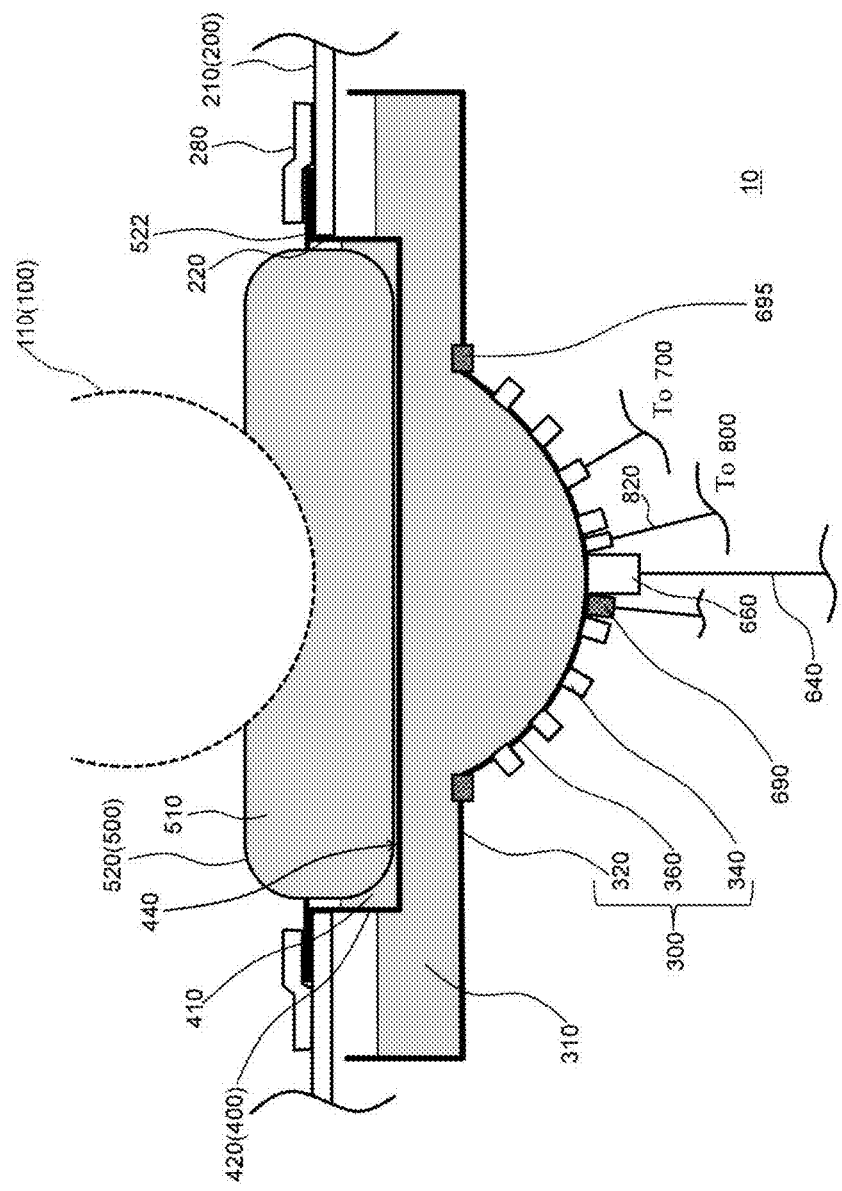
FIG. 2 is a partial enlargement of FIG. 1.
Figure 3A:
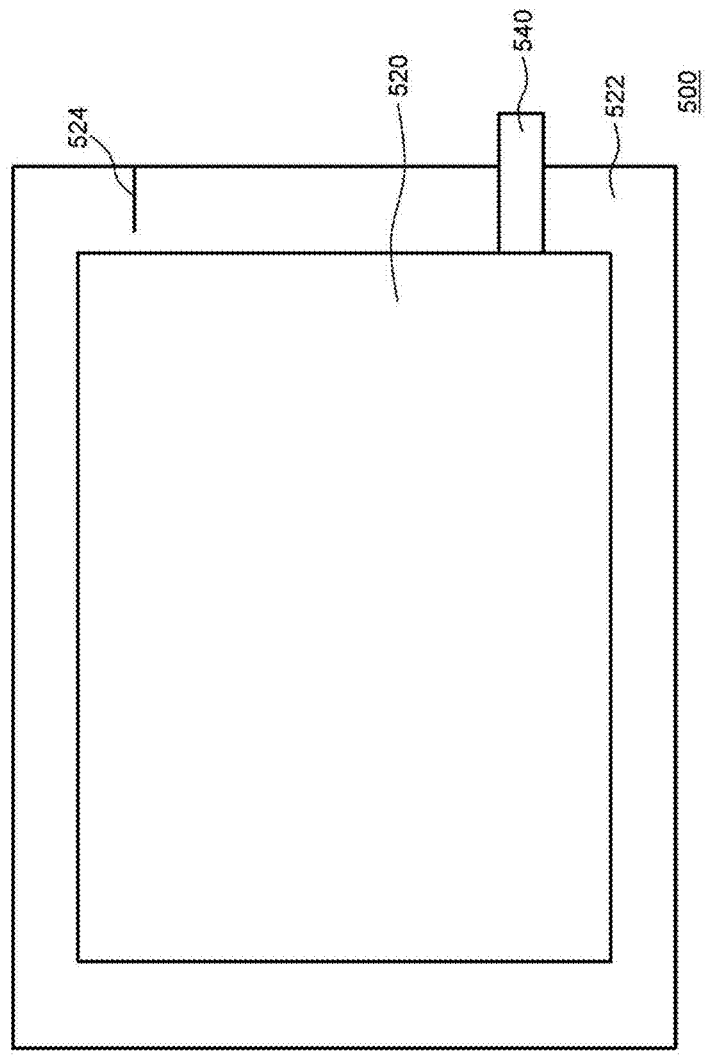
FIG. 3A is a schematic plan view of a matching-material bag.
Figure 3B:
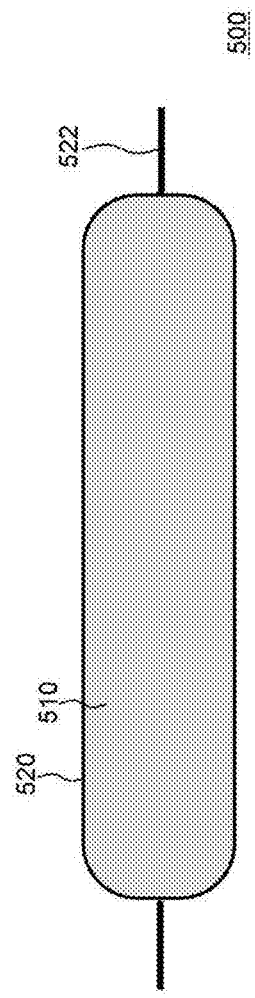
FIG. 3B is a schematic cross-sectional view of the matching-material bag.

An acoustic-wave measuring device 10 of the present embodiment will be described with reference to FIGS. 1 to 3B. FIG. 1 is a schematic diagram showing the acoustic-wave measuring device according to the present embodiment. FIG. 2 is a partial enlargement of FIG. 1. Note that FIGS. 1 and 2 omit portions of an examination subject 100 other than an examination site 110. FIGS. 3A and 3B are a schematic plan view and a schematic cross-sectional view, respectively, of a matching-material bag.

The acoustic-wave measuring device 10 of the present embodiment is configured as a photoacoustic tomography (PAT) device (photoacoustic imaging device), for example. A PAT device irradiates a predetermined examination site of the examination subject with light, for example. After a tissue in the examination site absorbs the light, the portion that has absorbed the light releases heat and generates acoustic waves (compressional waves) due to volumetric expansion. This phenomenon is called the "photoacoustic effect", and acoustic waves generated due to the photoacoustic effect are also called "photoacoustic waves". These waves are also called "opto-ultrasonic waves". Characteristics information regarding the inside of the examination subject and a distribution thereof can be obtained by receiving photoacoustic waves generated due to the photoacoustic effect.

As shown in FIG. 2, the acoustic-wave measuring device 10 of the present embodiment includes, for example, a support table (base) 200, a receiving unit (detection unit) 300, a light source 620, an optical system 640, an imaging unit 690, a scanning mechanism (movement mechanism) 380, a placement unit 400, a matching-material bag 500, a supply unit 800, and a processing unit 700.

Note that the following "examination subject 100" refers to, for example, a living body (human body). A predetermined "examination site 110" of the examination subject 100 means an area from which acoustic waves are to be measured (detected) and is, for example, a hand, foot, face, trunk, breast, or the like.

Support Table

The support table 200 is configured as a base on which the examination subject 100 is placed, for example. Specifically, the support table 200 has a support surface 210 and an opening portion 220, for example.

The support surface 210 supports portions of the examination subject 100 other than the examination site 110, for example. A space is provided under the support surface 210 of the support table 200, and a later-described receiving unit 300 and other components are provided in this space.

The opening portion 220 is provided in the support surface 210 in order to measure the predetermined examination site 110 of the examination subject 100, for example. The opening portion 220 is wider than the examination site 110 in order to measure acoustic waves from the predetermined examination site 110. The planar shape of the opening portion 220 is a rectangle, for example.

In the present embodiment, a separation film 420 and a matching-material bag 500 can be installed on the support table 200, for example. This will be described later in detail.

Receiving Unit

The receiving unit 300 receives acoustic waves from the predetermined examination site 110 of the examination subject 100, for example. The receiving unit 300 of the present embodiment has a container 320, receiving elements (transducers, conversion elements) 340, and an element holder 360, for example.

Container

The container 320 is located vertically below the support surface 210, for example. The container 320 is configured to be capable of containing (storing) an acoustic matching material 310, for example.

The acoustic matching material 310 is in a liquid or gel form and has an acoustic impedance that matches the examination subject 100, for example. An acoustic impedance "matching the examination subject 100" as mentioned in the present embodiment includes not only the case of completely matching the acoustic impedance of the examination subject 100 but also the case of being close to the acoustic impedance of the examination subject 100 with a predetermined error. Specifically, "an acoustic impedance that matches the examination subject 100" is in the range of 0.5 times or more and 2 times or less the acoustic impedance of the examination subject 100, for example. Specific examples of the acoustic matching material 310 include water and oil.

The container 320 in the present embodiment contains the acoustic matching material 310 in a manner such that the acoustic matching material 310 is not fixed and can change shape, i.e., contains the acoustic matching material 310 in a flowable state, for example.

In the present embodiment, the container 320 is packed with the acoustic matching material 310 to a position at which the acoustic matching material 310 comes into contact with the later-described separation film 420. It is thus possible to keep air from entering the propagation path of acoustic waves from the examination site 110 to the receiving elements 340.

Receiving Element

The receiving elements 340 are located vertically below the support surface 210, for example. The receiving elements 340 receive acoustic waves generated from the examination site 110, for example.

The receiving elements 340 also convert the received acoustic waves to electrical signals, for example. The electrical signals obtained by converting acoustic waves will be hereinafter referred to as "acoustic signals". The receiving elements 340 can receive acoustic waves with frequencies of 100 kHz or more and 1000 MHz or less, for example. More preferably, the receiving elements 340 are capable of receiving acoustic waves having frequencies of 100 kHz or more and 50 MHz or less, for example. Specific examples of the receiving elements 340 include piezoelectric elements made of lead zirconate titanate (PZT) or the like, polymeric piezoelectric film materials such as polyvinylidene fluoride (PVDF), capacitive micromachine ultrasonic transducers (CMUTs), and Fabry-Perot interferometers.

In the present embodiment, a plurality of receiving elements 340 are provided, for example. The measurement accuracy can be increased by receiving acoustic waves with the plurality of receiving elements 340. For example, the position accuracy for measuring characteristics information regarding the inside of the examination site 110 can be increased.

Element Holder

The element holder 360 holds the plurality of receiving elements 340, for example. The element holder 360 has a hemispherical (bowl-like) shape that is concave vertically downward, for example. The "hemispherical shape" here means a perfect circle cut with a flat cross-section, an ellipse cut with a flat cross-section, or a shape close to either of these shapes with a predetermined error. The center angle of the spherical surface constituted by the element holder 360 is 140° or more and 180° or less, for example.

The element holder 360 holds the plurality of receiving elements 340 in an array along the hemispherical surface so that the directional axes of the respective receiving elements 340 converge at a region around the curvature center of the hemispherical surface, for example. This enables a high resolution in the region around the curvature center of the hemispherical surface.

In the present embodiment, the curvature center of the hemispherical surface of the element holder 360 is located within the examination site 110 when the examination site 110 is placed on the later-described matching-material bag 500, for example. This enables high-resolution measurement to be performed within the predetermined examination site 110.

The element holder 360 in the present embodiment is provided at a bottom portion of the container 320 and integrally fixed with the container 320, for example. The element holder 360 contains the aforementioned acoustic matching material 310. Thus, the receiving element 340 receives acoustic waves via the acoustic matching material 310.

In the present embodiment, the container 320 contains the acoustic matching material 310 in a flowable state, as mentioned above. Therefore, even if the element holder 360 has a complex shape, the element holder 360 can be tightly packed with the acoustic matching material 310 without allowing air to enter.

Light Source

The light source 620 is configured to irradiate the predetermined examination site 110 with light, for example. The light source 620 is configured to be capable of emitting pulsed light, for example. Specifically, the light source 620 is, for example, a laser, a light-emitting diode, or a flash lamp. Examples of the laser include a gas laser, a solid-state laser, a dye laser, and a semiconductor laser.

The light source 620 emits light under the conditions under which the photoacoustic effect can be obtained, for example.

The wavelength of the light emitted from the light source 620 is, for example, a wavelength that is absorbed by a predetermined absorber that constitutes a tissue of the examination site 110, and is a wavelength that can propagate to the inside of the examination site 110. Specifically, the wavelength of the light is 500 nm or more and 1200 nm or less, for example.

The light source 620 may be able to emit light with different wavelengths, for example. Irradiating the examination site 110 with light with different wavelengths enables a distribution of characteristics information to be obtained based on differences in the absorption coefficient among the different wavelengths. For example, an oxygen saturation distribution or the like can be obtained.

The pulse width of the light emitted from the light source 620 satisfies so-called thermal/stress confinement conditions. That is, the pulse width is a time duration according to which light irradiation ends before heat propagates and escapes from the predetermined absorber in the examination site 110, and is a time duration according to which light irradiation ends before acoustic waves pass through the absorber. Specifically, the pulse width is 1 ns or more and 100 ns or less, for example.

Optical System

The optical system 640 is configured to transmit light from the light source 620, for example. The optical system 640 includes optical components such as a lens and a mirror, an optical fiber cable, or the like, for example.

A light outlet 660 at a terminal of the optical system 640 is configured to emit light transmitted from the light source 620 toward the examination site 110. The light outlet 660 is provided at the bottom portion of the element holder 360, for example. The light outlet 660 is provided in the element holder 360 together with the receiving elements 340, thus enabling photoacoustic waves to be measured in a wide area of the examination site 110.

Imaging Unit

The imaging unit 690 is located vertically below the support surface 210 and is configured to images at least the examination site 110 from vertically below, for example. The imaging unit 690 is provided at the bottom portion of the element holder 360, for example.

The imaging unit 690 has a light 695 that irradiates the examination site 110 with light, for example. The light 695 has a ring shape and is provided along an outer edge (surrounding the outer edge) of the hemispherical element holder 360, for example.

As will be described later, the examination site 110 is covered with a screen (not shown) before a measurement step S300 to suppress leakage of light used in the measurement. Thus, the position of the examination site 110 can be adjusted even when it is covered with the screen by imaging the examination site 110 from vertically below with the imaging unit 690 while irradiating the examination site 110 with light with use of the light 695.

It is preferable that the imaging unit 690 in the present embodiment has a cut filter that cuts off the light from the light source 620, for example. This can suppress damage to the imaging unit 690 caused by the light from the light source 620.

Further, the imaging unit 690 in the present embodiment may also image the matching-material bag 500 from vertically below, for example. It is thus possible to check the position and state of the matching-material bag 500, the presence of bubbles between the matching-material bag 500 and the separation film 420, or the like.

Scanning Mechanism

The scanning mechanism 380 is configured to scan (move) the receiving elements 340 relative to the examination subject 100 placed on the support table 200, for example. The scanning mechanism 380 in the present embodiment is configured to scan the receiving unit 300 as an integral unit having the container 320 and the receiving elements 340, for example.

The scanning mechanism 380 is configured to scan the receiving elements 340 in at least one predetermined direction. The scanning mechanism 380 may scan the receiving elements 340 in two directions (X and Y directions) or three directions (X, Y, and Z directions), for example. The scanning mechanism 380 in the present embodiment is configured to scan the receiving elements 340 in the X and Y directions on a horizontal plane parallel with the support surface 210, for example.

In the present embodiment, the container 320 contains the acoustic matching material 310 in a flowable state, as mentioned above. This enables the receiving elements 340 to maintain the state of being in contact with the acoustic matching material 310 even if the scanning mechanism 380 scans the receiving unit 300.

Supply Unit

The supply unit 800 is configured to supply the acoustic matching material 310 into the container 320 via a supply tube 820, for example. The supply tube 820 is connected to a portion of the element holder 360, for example. The acoustic matching material 310 is supplied from the supply unit 800 so as to keep the upper surface of the acoustic matching material 310 in the container 320 at a predetermined position.

Processing Unit

The processing unit 700 is configured to control each part of the acoustic-wave measuring device 10 and process characteristics information regarding the inside of the examination site 110, for example.

The processing unit 700 is configured as a computer, for example. Specifically, the processing unit 700 has a central processing unit (CPU), a graphic processing unit (GPU), a random access memory (RAM), a storage device, and an I/O port, for example. The RAM, the storage device, and the I/O port can exchange data with the CPU. The I/O port is connected to each of the receiving elements 340 via a predetermined amplifier and signal processors such as an AD converter and an arithmetic circuit (not shown), and is connected to the light source 620, the imaging unit 690, the scanning mechanism 380, and the display unit 720, for example. The storage device stores a program related to acoustic wave measurement, characteristics information regarding the inside of the examination site 110, or the like. The storage device is, for example, a hard disk drive (HDD), a flash memory, or the like. The RAM temporarily retains information, a program, or the like that is read out from the storage device by the CPU. The CPU controls each part of the acoustic-wave measuring device 10 and processes characteristics information regarding the inside of the examination site 110 by executing a predetermined program stored in the storage device. The display unit 720 displays characteristics information regarding the inside of the examination site 110 obtained by executing the predetermined program, and images of the examination site 110 or the like obtained by the imaging unit 690, for example.

(2) Configuration Related to Acoustic Matching

A description will be given of the details of the configuration related to acoustic matching in the acoustic-wave measuring device 10 of the present embodiment, with reference to FIGS. 2 to 3B.

As a configuration related to acoustic matching, the acoustic-wave measuring device 10 of the present embodiment adopts a separated structure of "examination subject/matching-material bag/separation film/acoustic matching material/the receiving elements".

That is, the acoustic-wave measuring device 10 of the present embodiment is configured so that the separation film 420, which does not allow the acoustic matching material 310 to permeate, and the matching-material bag 500, which contains an acoustic matching material 510 in a liquid or gel form, are installable in this order between the acoustic matching material 310 contained in the container 320 and the examination site 110, as shown in FIG. 2, for example.

The matching-material bag 500 thus containing the acoustic matching material 510 for the subject 100 side enables both reducing the burden on the examination subject 100 and easily ensuring a clean state.

Note that "installable" here means that the separation film 420 and the matching-material bag 500 can be replaceably (removably) installed in (attached to) the acoustic-wave measuring device 10. In other words, it may be considered that the acoustic-wave measuring device 10 has an attachment portion (not denoted by a reference numeral) to which the separation film 420 and the matching-material bag 500 can be attached.

Placement Unit

As shown in FIG. 2, the placement unit 400 is configured to receive the matching-material bag 500 placed thereon, for example. The placement unit 400 in the present embodiment is configured to separate the examination subject 100 side from the receiving unit 300 side, for example.

The separation film 420, which is included in the placement unit 400, is configured not to allow the acoustic matching material 310 to permeate, for example. The separation film 420 is configured to allow the light from the light source 620 to pass, for example. Further, the separation film 420 has an acoustic impedance that matches the examination subject 100 so that acoustic waves from the examination site 110 can propagate, for example. Specifically, examples of the material of the separation film 420 that meets the aforementioned requirements include polyethylene terephthalate (PET) and polyethylene (PE).

The thickness of the separation film 420 is determined based on the frequency band of acoustic waves used to acquire characteristics information regarding the examination site 110 and the longitudinal wave velocity within the separation film 420. Here, the longitudinal wave velocity within the separation film 420 is about the same as the examination subject 100 as a typical living body, for example. Specifically, the longitudinal wave velocity within the separation film 420 is 1000 m/s or more and 2500 m/s or less, for example. Here, when characteristics information is acquired using acoustic waves in a frequency band of 1.5 MHz or less, it is preferable that the thickness of the separation film 420 is 1 mm or less, for example. When characteristics information is acquired using acoustic waves in a frequency band over 1.5 MHz and 10 MHz or less, it is preferable that the thickness of the separation film 420 is 0.15 mm or less, for example. When characteristics information is acquired using acoustic waves in a frequency band over 10 MHz and 50 MHz or less, it is preferable that the thickness of the separation film 420 is 0.03 mm or less, for example. If the thickness of the separation film 420 is out of the above range, there is a possibility that the signal intensity significantly drops at a specific frequency or a specific angle. In contrast, measurement accuracy can be increased by setting the thickness of the separation film 420 to a predetermined thickness or less in accordance with the frequency band of acoustic waves used to acquire characteristics information as mentioned above. Note that the higher the frequency band of acoustic waves used to acquire characteristics information, higher-resolution information can be acquired.

In the present embodiment, at least the separation film 420 of the placement unit 400 is replaceable (disposable), for example. Cross-infection between examination subjects 100 can be suppressed by replacing the separation film 420 when the examination subject 100 changes.

The placement unit 400 is arranged so as to block (cover) the opening portion 220 of the support table 200, for example. Specifically, the placement unit 400 is wider than the opening portion 220, for example. The placement unit 400 is fixed to the support surface 210 of the support table 200 by a predetermined attachment portion (not shown) around the opening portion 220, for example. This configuration can keep the examination subject 100 from coming into contact with the acoustic matching material 310 in the container 320.

The placement unit 400 has a recessed portion 440 having a tray shape that is recessed vertically downward of the support surface 210, for example. The aforementioned separation film 420 constitutes at least (a part of) the bottom portion of the recessed portion 440 within the opening portion 220. The separation film 420 is formed by pressure molding using the aforementioned material, for example.

The placement unit 400 being recessed vertically downward brings the separation film 420 that constitutes the placement unit 400 into contact with the acoustic matching material 310 contained in the container 320. This can keep air from entering between the separation film 420 and the acoustic matching material 310.

Further, the placement unit 400, which has the recessed portion 440, is configured to allow the later-described matching-material bag 500 to be accommodated in the recessed portion 440, for example. This enables the matching-material bag 500 to be stably accommodated (placed).

Since the separation film 420 that constitutes the placement unit 400 has the recessed portion 440, the separation film 420 of the placement unit 400 is capable of containing the matching liquid (acoustic matching liquid) 410 within the recessed portion 440, for example. The recessed portion 440 can suppress an outflow of the matching liquid 410 onto the support table 200.

The matching liquid 410 is in a liquid form, similarly to the acoustic matching material 310, and has an acoustic impedance that matches the examination subject 100, for example. The matching liquid 410 is, for example, water, oil, or the like. Due to the matching liquid 410 being in close contact with the separation film 420 and the later-described matching-material bag 500, it is possible to keep air from entering between the separation film 420 and the matching-material bag 500.

The recessed portion 440 of the placement unit 400 is removably fitted to the opening portion 220 of the support table 200. The area of the recessed portion 440 of the placement unit 400 is almost the same as or slightly smaller than the area of the opening portion 220 of the support table 200, for example. This can keep the recessed portion 440 of the placement unit 400 from shifting in the opening portion 220 of the support table 200.

The depth of the recessed portion 440 of the placement unit 400 is determined based on the position of the upper surface of the matching-material bag 500 accommodated in the recessed portion 440, and is, for example, 30 mm or less, and preferably 20 mm or less. In the present embodiment, the depth of the recessed portion 440 is 10 mm, for example. Thus setting the depth of the recessed portion 440 to 30 mm or less can alleviate pain felt by the person who is the examination subject 100. This point will be described later.

Matching-Material Bag

As shown in FIGS. 2 to 3B, the matching-material bag 500 contains the acoustic matching material 510, for example. The acoustic matching material 510 is in a liquid or gel form, similarly to the acoustic matching material 310, and has an acoustic impedance that matches the examination subject 100, for example. The acoustic matching material 510 is, for example, water, oil, or the like.

The matching-material bag 500 is arranged (placed) on the placement unit 400 and interposed between the placement unit 400 and the examination subject 100, for example. The matching-material bag 500 being interposed between the placement unit 400 and the examination subject 100 with the acoustic matching material 510 contained in the matching-material bag 500 can keep the examination subject 100 from coming into direct contact with the acoustic matching material 510 while keeping air from entering between the placement unit 400 and the examination subject 100.

When there is a possibility that air enters between the matching-material bag 500 and the examination site 110, a small amount of acoustic matching material may further be tightly interposed therebetween. This can suppress the presence of air that cannot be fully eliminated by the matching-material bag 500 conforming to the examination site 110. The acoustic matching material in this part is in a liquid or gel form, and has an acoustic impedance that matches the examination subject 100, for example. The acoustic matching material is, for example, water, oil, a hydrophilic solution, or the like. Examples of the provision method include spraying and application. Note that the amount of acoustic matching material interposed between the matching-material bag 500 and the examination site 110 is small, thus reducing the burden on the examination subject 100.

The matching-material bag 500 is flexible, for example. The matching-material bag 500 can thus follow the shape of the examination site 110. As a result, air can be stably kept from entering between the examination site 110 and the surface of the matching-material bag 500.

The matching-material bag 500 in the present embodiment is separable from the separation film 420 and replaceable (disposable) together with the acoustic matching material 510, for example. The examination site 110 can always be placed on the matching-material bag 500 in a clean state by replacing the matching-material bag 500 when the examination subject 100 changes.

In the present embodiment, the matching-material bag 500 is installable so that the upper surface of the matching-material bag 500 is at least partially located at the same height as the support surface 210 or vertically above the support surface 210, at least in a state where the examination subject 100 is placed on the support surface 210 of the support table 200 (i.e., the examination site 110 is placed on the matching-material bag 500). This can keep stress from concentrating at a step at a peripheral end of the opening portion 220 of the support surface 210 due to the load of the examination subject 100.

Further, it is preferable in the present embodiment that the matching-material bag 500 is installable so that the upper surface of the matching-material bag 500 is at least partially located at the same height as the support surface 210 or vertically above the support surface 210 in the state where the examination subject 100 is not placed on the support surface 210 of the support table 200 (i.e., in a state before the examination site 110 is placed on the matching-material bag 500). This can reliably keep stress from concentrating at a step at a peripheral end of the opening portion 220 of the support surface 210 due to the load of the examination subject 100.

Next, a specific configuration of the matching-material bag 500 will be described with reference to FIGS. 3A and 3B. As shown in FIGS. 3A and 3B, the matching-material bag 500 has a bag body 520 and an inlet 540, for example.

The bag body 520 includes a bag-shaped film having a storage space (storage area, a reference numeral of which is not shown) for containing the acoustic matching material 510, for example. The film constituting the bag body 520 is configure not to allow the acoustic matching material 510 to permeate (leak out), for example. Also, the film is configured to allow the light from the light source 620 to pass, for example. Further, the film has an acoustic impedance that matches the examination subject 100 so that acoustic waves from the examination site 110 can propagate, for example. Specifically, examples of the material of the film that meets the aforementioned requirements include polyethylene, polyurethane, polyethylene terephthalate, nylon, and laminates thereof.

The thickness of the film that constitutes the bag body 520 is determined based on the frequency band of acoustic waves used to acquire characteristics information regarding the examination site 110 and the longitudinal wave velocity within the film that constitutes the bag body 520, in the same manner as the thickness of the separation film 420. Here, the longitudinal wave velocity within the film that constitutes the bag body 520 is about the same as that within the examination subject 100, which is a typical living body, as with the aforementioned separation film 420, for example. Specifically, the longitudinal wave velocity within the film that constitutes the bag body 520 is 1000 m/s or more and 2500 m/s or less, for example. Here, the thickness of the film that constitutes the bag body 520 can be in the same range as the thickness of the aforementioned separation film 420, for example, in accordance with the frequency band of acoustic waves used to acquire characteristics information. This can increase measurement accuracy. For example, a required resolution can be obtained by setting the thickness of a film made of polyurethane or polyethylene to 25 μm or less.

For example, a portion of the bag body 520 that constitutes the storage space is placed in the recessed portion 440 of the placement unit 400, while the peripheral part of the bag body 520 that surrounds the storage space is placed on the support surface 210 of the support table 200.

The bag body 520 has, for example, a fixation margin (edge portion, frame portion, ear portion) 522 and a slit portion 524 in a peripheral part that surrounds the storage space.

The fixation margin 522 surrounds the storage space and can be fixed to the support table 200 with later-described fixing members 280, for example. Specifically, the fixation margin 522 is made by, for example, overlaying a pair of films that constitute the bag body 520 and heat-sealing the films in a frame shape to demarcate the storage space. Thus fixing the fixation margin 522 using the fixing members 280 enables the matching-material bag 500 to be stably fixed to the support table 200.

The fixation margin 522 may have a higher strength than the portion constituting the storage space, for example. Specifically, the entire fixation margin 522 may be heat-sealed. This can suppress a breakage or the like of the films that constitute the bag body 520.

The slit portion 524 is formed from the outer edge of the fixation margin 522 toward the storage space, for example. The acoustic matching material 510 in the storage space can be easily discharged from the matching-material bag 500 by tearing the slit portion 524 when the matching-material bag 500 is replaced.

The inlet 540 brings the outer edge of the bag body 520 into communication with the inside (storage area) and is configured to allow the acoustic matching material 510 to be injected into the storage space in the matching-material bag 500, for example. The acoustic matching material 510 is thus injected via the inlet 540, thereby suppressing leakage of the acoustic matching material 510. It is preferable that the inlet 540 is configured as a check valve that allows the acoustic matching material 510 to be irreversibly injected into the matching-material bag 500, for example. This can suppress leakage of the acoustic matching material 510 from the inlet 540.

The inlet 540 is flexible, for example. Specifically, the inlet 540 is formed with a film, similarly to the bag body 520, for example. Note that the material and the thickness of the film that constitutes the inlet 540 may be the same as or different from the material and the thickness of the film that constitutes the bag body 520. The inlet 540 in the present embodiment is constituted by a film as mentioned above, and is, therefore, not constituted by a solid tool such as a spout or a connector. This can keep stress from concentrating at the inlet 540 due to the load of the examination subject.

Fixing Member

As shown in FIG. 2, the aforementioned matching-material bag 500 is configured to be capable of being fixed to the support table 200 with use of predetermined fixing members 280, for example.

Specifically, each fixing member 280 is configured as a binder (clip) that is provided on the support surface 210 of the support table 200 and elastically holds the fixation margin 522 of the matching-material bag 500 from opposite sides, for example. For example, four fixing members 280 are provided. The four fixing members 280 are symmetrically arranged with respect to the center of the opening portion 220 of the support table 200, at the periphery of the opening portion 220, for example. This configuration enables the matching-material bag 500 to be stably fixed to the support surface 210.

(3) Acoustic Wave Measurement Method

An acoustic wave measurement method according to the present embodiment will be described with reference to FIGS. 1 and 2.

The acoustic wave measurement method of the present embodiment includes a preparation step S100, a placement step S200, a measurement step S300, and an end-determination step S400 in this order, for example.

S100: Preparation Step

First, the above-described acoustic-wave measuring device 10 having the support table 200, the container 320, the receiving elements 340, and so on, is prepared as shown in FIG. 2.

The container 320 contains the acoustic matching material 310 in a flowable state. The container 320 is packed with the acoustic matching material 310 to a position at which the acoustic matching material 310 comes into contact with the separation film 420.

With the container 320 containing the acoustic matching material 310, the separation film 420 and the matching-material bag 500 containing the acoustic matching material 510 are installed in this order between the acoustic matching material 310 contained in the container 320 and the examination site 110.

Specifically, the placement unit 400 is arranged so as to block the opening portion 220 of the support table 200. After the placement unit 400 has been arranged, the frame portion of the placement unit 400 is fixed to the support surface 210 of the support table 200 using a predetermined attachment portion. After the placement unit 400 has been fixed to the support table 200, the matching liquid 410 is put into the recessed portion 440 of the placement unit 400. In the present embodiment, merely a small amount of matching liquid 410 is sufficient since the matching-material bag 500 is used.

Meanwhile, the matching-material bag 500 is prepared. The acoustic matching material 510 is injected into the storage space in the matching-material bag 500 via the inlet 540.

After the arrangement of the placement unit 400 and the preparation of the matching-material bag 500 has been completed, the matching-material bag 500 into which the acoustic matching material 510 has been injected is placed in the recessed portion 440 of the placement unit 400.

Here, in the present embodiment, the matching-material bag 500 is arranged so that the upper surface of the matching-material bag 500 is at least partially located at the same height as the support surface 210 or vertically above the support surface 210, at least when the examination subject 100 is placed on the support surface 210 of the support table 200. Further, in the present embodiment, it is preferable that the matching-material bag 500 is installed so that the upper surface of the matching-material bag 500 is at least partially located at the same height as the support surface 210 or vertically above the support surface 210 when the examination subject 100 has not been placed on the support surface 210 of the support table 200 (i.e., at the stage of the preparation step S100).

Specifically, the depth of the recessed portion 440 of the placement unit 400 and the height of the matching-material bag 500 containing the acoustic matching material 510 are set to meet the aforementioned requirement regarding the upper surface of the matching-material bag 500, for example. Alternatively, the amount of acoustic matching material 510 to be injected into the matching-material bag 500 may be adjusted with the depth of the recessed portion 440 of the placement unit 400 fixed to a predetermined depth, for example, to meet the aforementioned requirement regarding the upper surface of the matching-material bag 500. Note that, here, the height of the upper surface of the matching-material bag 500 may also be varied by adjusting the amount of acoustic matching material 510 to be injected into the matching-material bag 500 in accordance with the examination subject 100 and the examination site 110.

After the matching-material bag 500 has been installed, the fixation margin 522 of the matching-material bag 500 is fixed to the support table 200 using the fixing members 280.

S200: Placement Step

Next, the examination subject 100 is placed on the support surface 210 of the support table 200, and the examination site 110 is placed on the matching-material bag 500.

Here, when there is a possibility that air enters between the matching-material bag 500 and the examination site 110, a small amount of acoustic matching material may further be tightly interposed therebetween. For example, the acoustic matching material is added to at least either the matching-material bag 500 or the examination site 110 by means of spraying or application. After the acoustic matching material has been added, the examination site 110 is placed on the matching-material bag 500.

After the examination subject 100 has been placed, a screen (not shown) is put over the examination site 110. This can suppress leakage of the light used in the measurement.

S300: Measurement Step

Next, the measurement step S300 is performed to receive acoustic waves generated from the predetermined examination site 110 of the examination subject 100, using the receiving elements 340.

In the measurement step S300 of the present embodiment, characteristics information regarding the inside of the examination subject 100 and a distribution thereof are acquired by receiving photoacoustic waves generated due to the photoacoustic effect through the following procedure. In the following, the processing unit 700 controls each part of the acoustic-wave measuring device 10 and processes the characteristics information.

First, the examination site 110 is irradiated with light from the light source 620 via the optical system 640. Upon a predetermined absorber of a tissue in the examination site 110 absorbing the irradiated light, the absorber that has absorbed the light releases heat and generates acoustic waves due to volume expansion. The receiving elements 340 receive the acoustic waves that are thus generated from the examination site 110. Upon the receiving elements 340 receiving the acoustic waves, the receiving elements 340 converts the received acoustic waves to acoustic signals, which are electrical signals.

The processing unit 700 acquires characteristics information regarding the inside of the examination site 110 based on the acoustic signals obtained from the receiving elements 340. Examples of the specific characteristics information include the location of the source of the acoustic waves, the initial sound pressure in the examination site 110, the energy absorption density and absorption coefficient that are obtained based on the initial sound pressure, and the concentration of the substance constituting the tissue of the examination site 110.

Further, a two- or three-dimensional characteristics information distribution is acquired, and image data is generated as the characteristics information distribution based on characteristics information at each position within the examination site 110. Examples of the specific characteristics information distribution include, for example, initial sound pressure distribution, energy absorption density distribution, absorption coefficient distribution, and oxygen saturation distribution. Examples of the image reconstruction method for generating image data include universal back projection (UBP), filtered back projection (FBP), and delay and sum. The generated image data may also be subjected to predetermined image processing. After the image data has been obtained, the image data is displayed on the display unit 720.

Here, the scanning mechanism 380 moves the receiving unit 300 having the plurality of receiving elements 340 relative to the examination subject 100 while the plurality of receiving elements 340 each receive an acoustic wave from a corresponding position in the examination site 110 and converts the received acoustic wave to an acoustic signal. Image data is generated as a characteristics information distribution based on the thus-obtained acoustic signals. This can suppress artifacts occurring in the image data.

S400: End-Determination Step

After the measurement of the predetermined examination site 110 in the above examination subject 100 has ended, it is determined whether or not to perform the same measurement as above on another examination subject 100.

When a new examination subject 100 other than the previous one is measured, the matching-material bag 500 and the separation film 420 used in the previous measurement are discarded and replaced with a clean new matching-material bag 500 and separation film 420. After the matching-material bag 500 and the separation film 420 have been replaced, the above-described placement step S200 and measurement step S300 are performed on the new examination subject 100.

On the other hand, measurement ends when no other examination subject 100 is measured.

The acoustic wave measurement step of the present embodiment thus ends.

(4) Effects Achieved by the Present Embodiment

According to the present embodiment, the following one or more effects are achieved.

(a) As a configuration related to acoustic matching, the acoustic-wave measuring device 10 of the present embodiment adopts a separated structure of "examination subject/matching-material bag/separation film/acoustic matching material/receiving elements". That is to say, the acoustic-wave measuring device 10 of the present embodiment is configured so that the separation film 420 and the matching-material bag 500 containing the acoustic matching material 510 are installable in this order between the acoustic matching material 310 contained in the container 320 and the examination site 110.

The matching-material bag 500 being interposed between the placement unit 400 and the examination subject 100 with the acoustic matching material 510 contained in the matching-material bag 500 can keep the examination subject 100 from coming into direct contact with the acoustic matching material 510 while keeping air from entering between the placement unit 400 and the examination subject 100. This can keep the examination site 110 from being wetted by the acoustic matching material 510, for example. Further, it is also possible to keep examination clothes, a screen, or the like from being wetted, and to suppress deterioration of the measurement environment, for example. As a result, the burden on the examination subject 100 can be reduced.

Since the acoustic matching material 510 for the examination subject 100 side is contained in the matching-material bag 500, it is possible, when the examination subject 100 changes, to immediately discard the matching-material bag 500 and the separation film 420 used in the previous measurement and replace them with a matching-material bag 500 and a separation film 420 that are new and clean. Replacing the matching-material bag 500 and the separation film 420 when the examination subject 100 changes allows the examination site 110 to be always placed on a clean matching-material bag 500, and can suppress cross-infection between examination subjects 100.

As described above, according to the present embodiment, it is possible to achieve both reducing the burden on the examination subject 100 and easily ensuring a clean state while ensuring appropriate acoustic matching.

(b) In the present embodiment, the matching-material bag 500 can be installed so that the upper surface of the matching-material bag 500 is at least partially located at the same height as the support surface 210 or vertically above the support surface 210 at least in a state where the examination subject 100 is placed on the support surface 210 of the support table 200 (i.e., the examination site 110 is placed on the matching-material bag 500). This can keep the examination subject 100 from coming into contact with a step at a peripheral end of the opening portion 220 of the support surface 210. Stress concentration due to the load of the examination subject 100 can be suppressed by keeping the examination subject 100 from coming into contact with the step. Suppressing stress concentration makes it possible to stably reduce the burden on the examination subject 100 and keep the examination subject 100 from feeling pain. As a result, the measurement of acoustic waves can be stably continued.

(c) The placement unit 400 has a recessed portion 440 that is recessed vertically downward, for example. The separation film 420 at least constitutes the bottom portion of the recessed portion 440 within the opening portion 220.

The placement unit 400 being recessed vertically downward enables the separation film 420, which constitutes the placement unit 400, to easily come into contact with the acoustic matching material 310 contained in the container 320. This can keep air from entering between the separation film 420 and the acoustic matching material 310.

The placement unit 400 having the recessed portion 440 enables the matching-material bag 500 to be stably accommodated (placed) in the recessed portion 440 of the placement unit 400. This can suppress a shift of the matching-material bag 500.

Further, the placement unit 400 having the recessed portion 440 enables the matching liquid 410 to be contained in the recessed portion 440 of the placement unit 400. This allows the matching liquid 410 to be tightly interposed between the separation film 420 and the matching-material bag 500 and can keep air from entering therebetween. As a result, it is possible to suppress a decrease in the accuracy of acoustic wave measurement due to the presence of air.

(d) The matching-material bag 500 is configured to be capable of being fixed to the support table 200 using the predetermined fixing members 280. Fixing the matching-material bag 500 to the support table 200 can suppress a shift of the matching-material bag 500 even if the examination subject 100 moves. Suppressing a shift of the matching-material bag 500 can keep the matching-material bag 500 from wrinkling. Keeping the matching-material bag 500 from wrinkling can keep air from entering and suppress a change in the thickness of the matching-material bag 500 due to wrinkling of the matching-material bag 500. As a result, it is possible to suppress a decrease in the accuracy of acoustic wave measurement.

(5) Variations of First Embodiment

The above embodiment can be changed as in the following variations, as necessary. In the following, only elements different from the above embodiment will be described, and elements substantially identical to those described in the above embodiment will be assigned the same reference numerals and will not be described.

Variation 1-1

An acoustic-wave measuring device 10 of a variation 1-1 of the present embodiment will be described with reference to FIG. 4. FIG. 4 is a schematic enlarged view of a part of the acoustic-wave measuring device according to the variation 1-1 of the present embodiment.

The above embodiment has described the case where the placement unit 400 is constituted by the separation film 420, but the placement unit 400 may also have a holder mesh 460 and a frame body 480 as in the following variation 1-1. This enables the matching-material bag 500 and the examination site 110 to be held more stably. The acoustic-wave measuring device 10 of the variation 1-1 is different from the above embodiment in the configuration of the placement unit 400.

As shown in FIG. 4, the holder mesh 460 is arranged vertically below (in contact with) the separation film 420 and is configured to hold the matching-material bag 500 and the predetermined examination site 110 of the examination subject 100, for example. Specifically, the holder mesh 460 is configured to withstand the total weight of the examination site 110, the matching-material bag 500, and the separation film 420, for example. The holder mesh 460 is in the net form and is configured to allow at least part of the light from the light source 620 to pass, for example. The examination subject holder allows propagation (passage) of at least some of the acoustic waves from the examination site 110, for example. Examples of the material of the holder mesh 460 include polyester.

The frame body 480 is configured as a plate-like frame body that surrounds and holds the holder mesh 460, for example. The frame body 480 of the present embodiment has a lower frame 482, an upper frame 484, and a cushion material 488, for example.

The lower frame 482 has a rectangular shape in a plan view and constitutes a side portion of the aforementioned recessed portion 440, for example. The lower frame 482 is made of lightweight metal, such as aluminum, for example. The holder mesh 460 is fixed to a lower surface of the lower frame 482. For example, the holder mesh 460 is adhered to the lower surface of the lower frame 482 by means of an adhesive.

The lower frame 482 has a groove 482*a* in its upper surface, for example. The cushion material 488 attached to the later-described upper frame 484 is fitted into the groove 482*a*.

The lower frame 482 is arranged so as to allow the holder mesh 460 to be locked to the support table 200, for example. Specifically, the support table 200 has a locking portion (locking claw) 222 in the opening portion 220, for example. The lower frame 482 is removably fitted into the opening portion 220 and locked at the locking portion 222 of the support table 200 while holding the holder mesh 460, for example.

The upper frame 484 has a rectangular shape in a plan view, similarly to the lower frame 482, and is fixed onto the lower frame 482, for example. The upper frame 484 and the lower frame 482 hold the separation film 420 therebetween, for example. Specifically, the separation film 420 extends from the opening of the upper frame 484 and is folded around the upper surface, the outer side face, and the lower surface of the upper frame 484 in this order so as to surround the upper frame 484. The portion of the separation film 420 that is folded and comes into contact with the lower surface of the upper frame 484 is held between the upper frame 484 and the lower frame 482.

The cushion material 488 is attached to the lower surface of the upper frame 484, for example. The cushion material 488 attached to the upper frame 484 is configured to be capable of being fitted into the groove 482*a* in the lower frame 482. Due to the cushion material 488 coming into contact with the bottom face of the groove 482*a* in the lower frame 482, it is possible to keep the acoustic matching material 310 in the container 320 from making waves, rising, and leaking out from a gap between the separation film 420 and the lower frame 482 when the scanning mechanism 380 scans the receiving unit 300.

The aforementioned holder mesh 460 and frame body 480 are in contact with the acoustic matching material 310 in the container 320, and there is, therefore, a concern that the load-carrying capacity of the holder mesh 460 may deteriorate after long-term use. For this reason, the holder mesh 460 and the frame body 480 are configured to be capable of being replaced at the timing of predetermined periodic maintenance.

Effects

In the variation 1-1, the matching-material bag 500 and the predetermined examination site 110 of the examination subject 100 can be stably held by providing the holder mesh 460. Further, it has been confirmed that the holder mesh 460 in the net form is unlikely to affect the reception of ultrasonic waves. This holder mesh 460 is excellent in terms of the aforementioned holding stability and high-quality image obtainability.

Variation 1-2

Figure 5:
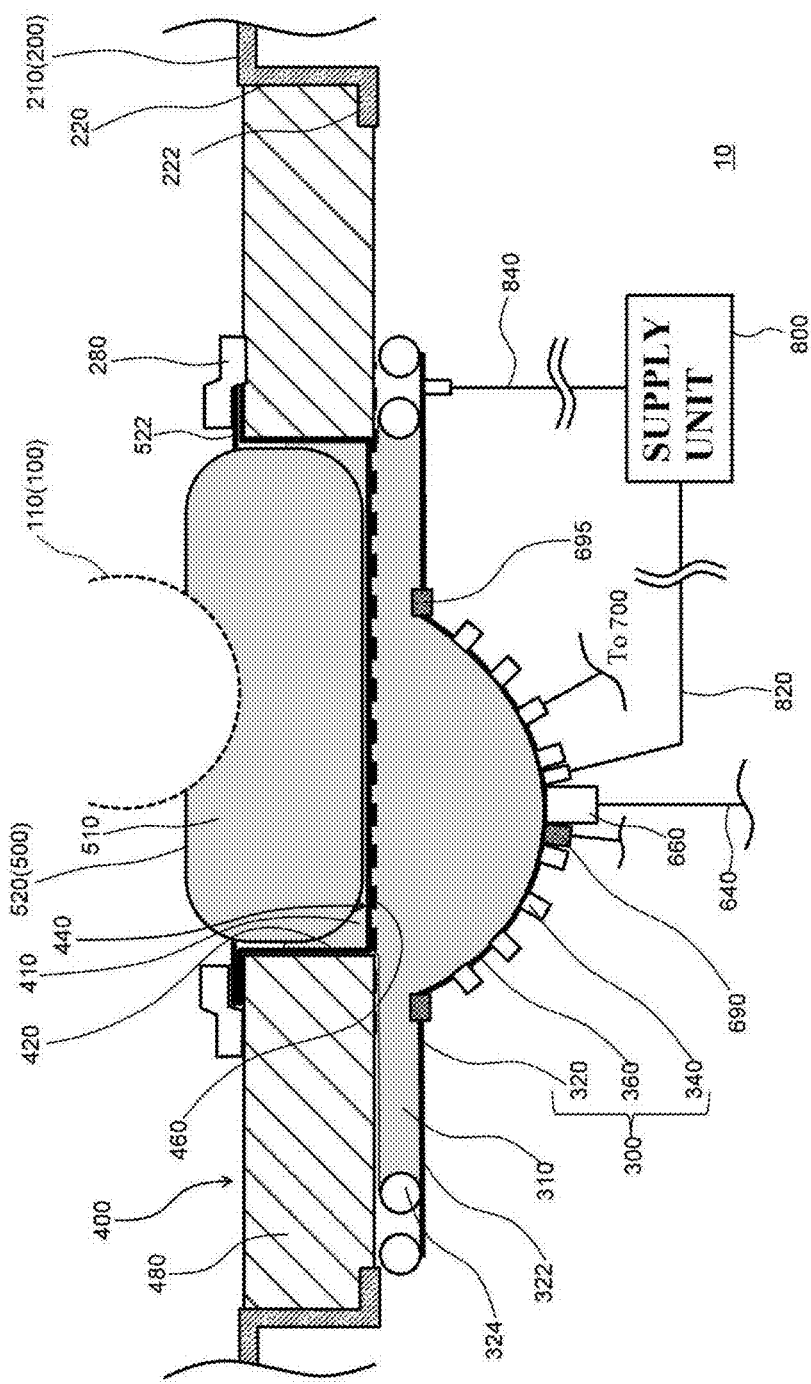
FIG. 5 is a schematic enlarged view of a part of an acoustic-wave measuring device according to a variation 1-2 of the first embodiment of the present invention.

An acoustic-wave measuring device 10 of a variation 1-2 of the present embodiment will be described with reference to FIG. 5. FIG. 5 is a schematic enlarged view of a part of the acoustic-wave measuring device according to the variation 1-2 of the present embodiment.

The acoustic-wave measuring device 10 of the variation 1-2 is different from the above embodiment in the configuration of the container 320 and the placement unit 400.

As shown in FIG. 5, the container 320 of this variation has a container bottom portion 322 and a rubber side portion 324, for example. The container bottom portion 322 has an element holder 360, and the portion other than the element holder 360 in the container bottom portion 322 has a flat plate shape, for example. The rubber side portion 324 is made of rubber that does not allow the acoustic matching material 310 to permeate, and surrounds the container bottom portion 322, for example. The rubber side portion 324 is double-layered, for example.

In this variation, for example, a discharge pipe 840 is connected between the two layers of the rubber side portion 324, and the supply unit 800 is connected via the discharge pipe 840. The supply unit 800 is configured to fill the container 320 with the acoustic matching material 310 to the top limit at which the acoustic matching material 310 does not leak from the inner rubber side portion 324, for example. Meanwhile, the supply unit 800 is configured to return the portion of the acoustic matching material 310 that overflows from the inner rubber side portion 324 via the discharge pipe 840, for example. The acoustic matching material 310 returned via the discharge pipe 840 is reused to supply the acoustic matching material 310 into the container 320.

The placement unit 400 of the present variation has a separation film 420, a holder mesh 460, and a frame body 480, for example.

The separation film 420 is configured not to allow the acoustic matching material 310 to permeate and constitutes a recessed portion 440 that is recessed vertically downward within the opening portion 220, as in the above embodiment, for example. The separation film 420 is made of the same material as in the above embodiment and is formed by pressure molding, for example.

The holder mesh 460 is arranged vertically below (in contact with) the separation film 420 and holds the matching-material bag 500 and the predetermined examination site 110 of the examination subject 100, for example. Specifically, the holder mesh 460 is configured to withstand the total weight of the examination site 110, the matching-material bag 500, and the separation film 420, for example. The holder mesh 460 is in the net form and allows at least part of the light from the light source 620 to pass, for example. The examination subject holder is configured to allow propagation (passage) of at least some of the acoustic waves from the examination site 110, for example. Examples of the material of the holder mesh 460 include polyester.

The frame body 480 is configured as a plate-like frame body that holds the holder mesh 460 in a surrounding manner, for example. The frame body 480 is made of lightweight metal such as aluminum, for example. The holder mesh 460 is fixed to the lower surface of the frame body 480. For example, the holder mesh 460 is adhered to the lower surface of the frame body 480 by an adhesive.

The frame body 480 is arranged so that the holder mesh 460 is locked to the support table 200, for example. Specifically, the support table 200 has a locking portion (locking claw) 222 in the opening portion 220, for example. The frame body 480 is removably fitted into the opening portion 220 and locked to the locking portion 222 of the support table 200 while holding the holder mesh 460, for example.

The aforementioned holder mesh 460 and frame body 480 are in contact with the acoustic matching material 310 in the container 320, and there is, therefore, a concern that the load-carrying capacity of the holder mesh 460 may deteriorate after long-term use. For this reason, the holder mesh 460 and the frame body 480 are configured to be capable of being replaced at the timing of predetermined periodic maintenance.

The matching-material bag 500 is placed on the separation film 420, as in the above embodiment, for example. The matching-material bag 500 is fixed to the frame body 480 using the fixing members 280 and is fixed to the support table 200 via the frame body 480, for example.

The acoustic-wave measuring device 10 of the present variation is configured so that the holder mesh 460, the lower surface of the frame body 480, and the upper surface of the acoustic matching material 310 in the container 320 are capable of being brought close to each other to allow the acoustic matching material 310 in the container 320 to block holes in the holder mesh 460.

The separation film 420 does not protrude vertically downward of the lower surface of the frame body 480 and does not sink in the acoustic matching material 310 in the container 320. Meanwhile, the acoustic matching material 310 in the container 320 blocks the holes in the holder mesh 460 and is in contact with (sticks to) the separation film 420.

When, for example, the size of each hole in the holder mesh 460 is small, the acoustic matching material 310 blocks the holes in the holder mesh 460 and comes into contact with the separation film 420 as a result of the upper surface of the acoustic matching material 310 in the container 320 rising due to the capillary phenomenon. In contrast, when, for example, the size of each hole in the holder mesh 460 is large, the aforementioned capillary phenomenon does not occur, but the acoustic matching material 310 is continuously supplied from the supply unit 800 to the container 320. Therefore, the acoustic matching material 310 keeps blocking the holes in the holder mesh 460 and in contact with the separation film 420. Thus, bubbles (an air layer) are kept from entering between the separation film 420, the holder mesh 460, and the acoustic matching material 310 in the container 320, regardless of the size of each hole in the holder mesh 460.

Effects

In the variation 1-2, the holder mesh 460, the lower surface of the frame body 480, and the upper surface of the acoustic matching material 310 in the container 320 can be brought close to each other so that the acoustic matching material 310 in the container 320 blocks the holes in the holder mesh 460. Thus, in the measurement step S300, the resistance of the acoustic matching material 310 caused by the separation film 420, the holder mesh 460, and the frame body 480 can be reduced when the scanning mechanism 380 moves the receiving unit 300 having the plurality of receiving elements 340 relative to the examination subject 100. Reducing the resistance of the acoustic matching material 310 enables the receiving unit 300 to move smoothly and rapidly. As a result, the measurement step S300 can be performed stably and rapidly.

Second Embodiment of the Present Invention

Next, the second embodiment of the present invention will be described. In the following, description will be omitted as appropriate, as in the variations of the above-described first embodiment.

(1) New Findings

The inventors further examined the device according to the above-described first embodiment and made the following new findings.

Figure 14:
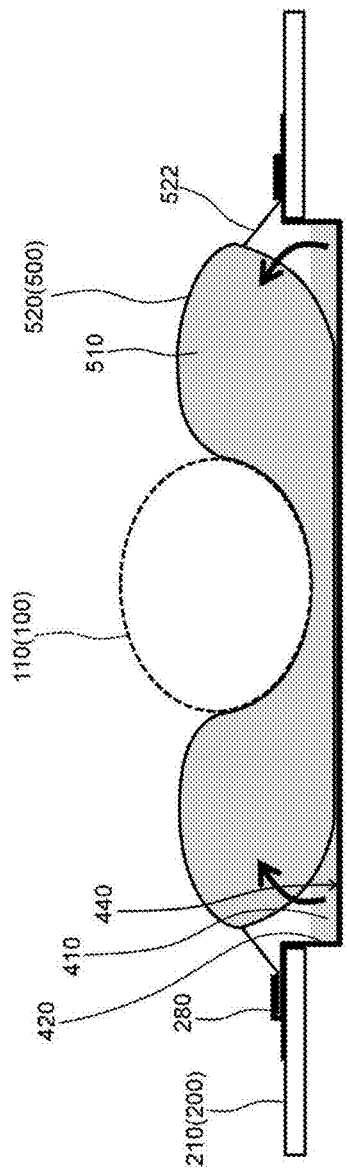
FIG. 14 is a diagram showing the state where an examination site is placed on a matching-material bag in an acoustic-wave measuring device according to a reference example.

The new findings regarding the device according to the above-described first embodiment will be described with reference to FIG. 14. FIG. 14 shows an examination site placed on a matching-material bag in an acoustic-wave measuring device according to a reference example.

(i) Upper Corner Portions of Recessed Portion

As shown in FIG. 14, a placement unit 400 in the reference example has upper corner portions of a recessed portion 440 whose angle is, for example, a right angle. In this case, when an examination site 110 is placed on a matching-material bag 500, there is a possibility that the examination site 110 comes into contact with the upper corner portions of the recessed portion 440 depending on, for example, the weight of the examination site 110 and the amount of acoustic matching material 510 in the matching-material bag 500. There is, therefore, a possibility that an examination subject 100 feels pain.

(ii) Rise of End Portion of Matching-Material Bag

When, as a reference example, the examination site 110 is placed on the matching-material bag 500 as shown in FIG. 14, there are cases where the examination site 110 sinks a large amount into the matching-material bag 500 depending on, for example, the weight of the examination site 110 and the amount of acoustic matching material 510 in the matching-material bag 500, and the like. In this case, the acoustic matching material 510 in the matching-material bag 500 moves outward of the examination site 110, causing the end portions of the matching-material bag 500 to rise. If the end portions of the matching-material bag 500 rise, the end portions of the matching-material bag 500 move away from the matching liquid 410 in the recessed portion 440, and a gap is generated therebetween. There is a possibility that the presence of such a gap impairs the matching of acoustic impedance with the examination subject 100 and makes it difficult to measure acoustic waves stably.

(iii) Overflow of Acoustic Matching Material

In contrast to the above item (ii), it is conceivable to tightly lay the matching-material bag 500 in the recessed portion 440 of the placement unit 400. However, in this case, the volume between the recessed portion 440 of the placement unit 400 and the matching-material bag 500 becomes smaller. There is, therefore, a possibility that the matching liquid 410 overflows from the recessed portion 440 when, for example, the matching-material bag 500 is placed in the recessed portion 440 or when the examination site 110 is placed on the matching-material bag 500. As a result, there is a possibility that the examination site 110 is wetted by the matching liquid 410 even though the matching-material bag 500 is used.

(iv) Contamination and Damage to Matching-Material Bag

As in the above embodiment, the matching-material bag 500 is replaced every time the examination subject 100 (person to be examined) changes, and it is, therefore, necessary to stock many unused matching-material bags 500 to measure a large number of people to be examined. Here, if many matching-material bags 500 are stored in a stacked state with their surfaces exposed, there is a possibility that the surfaces of the matching-material bags 500 are contaminated or damaged. In this case, there is a concern that the cleanliness and rigidity (shape stability) of the matching-material bags 500 may be impaired during measurement using the matching-material bags 500.

The following second embodiment is based on the above-described new findings made by the inventors etc.

(2) Acoustic-Wave Measuring Device

Figure 6:
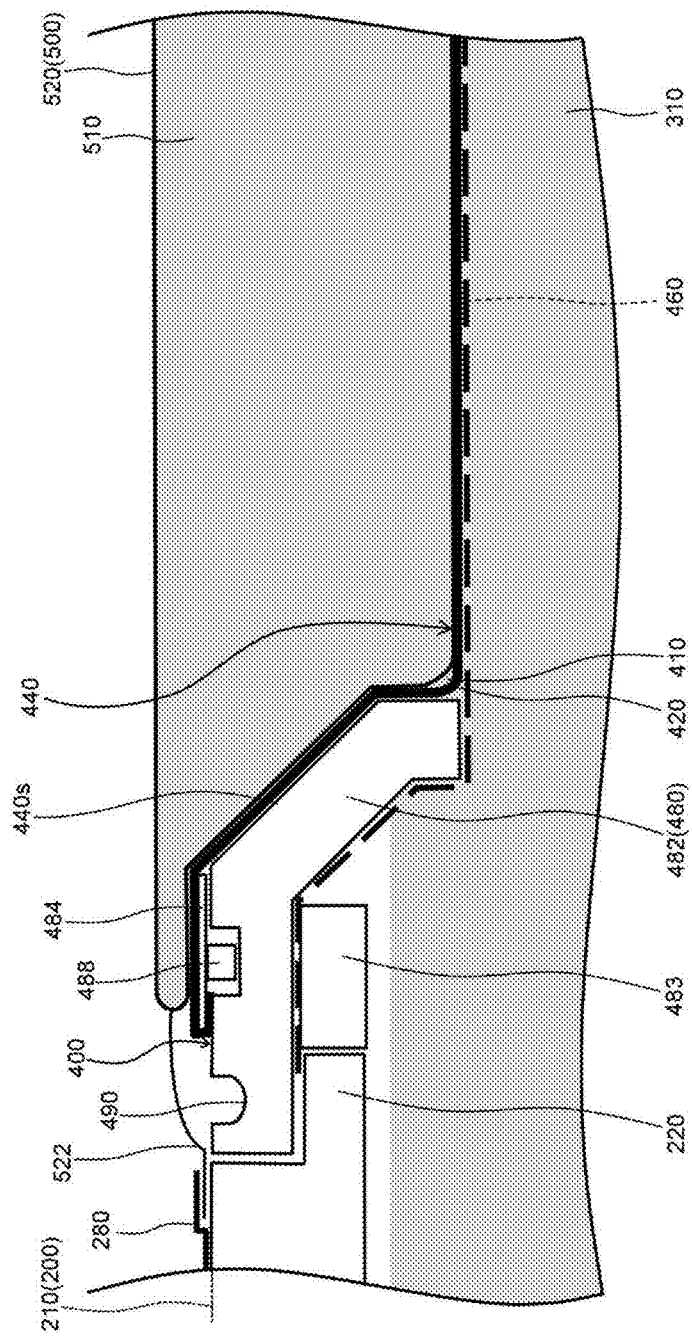
FIG. 6 is a schematic enlarged view of a part of an acoustic-wave measuring device according to a second embodiment of the present invention.
Figure 7A:
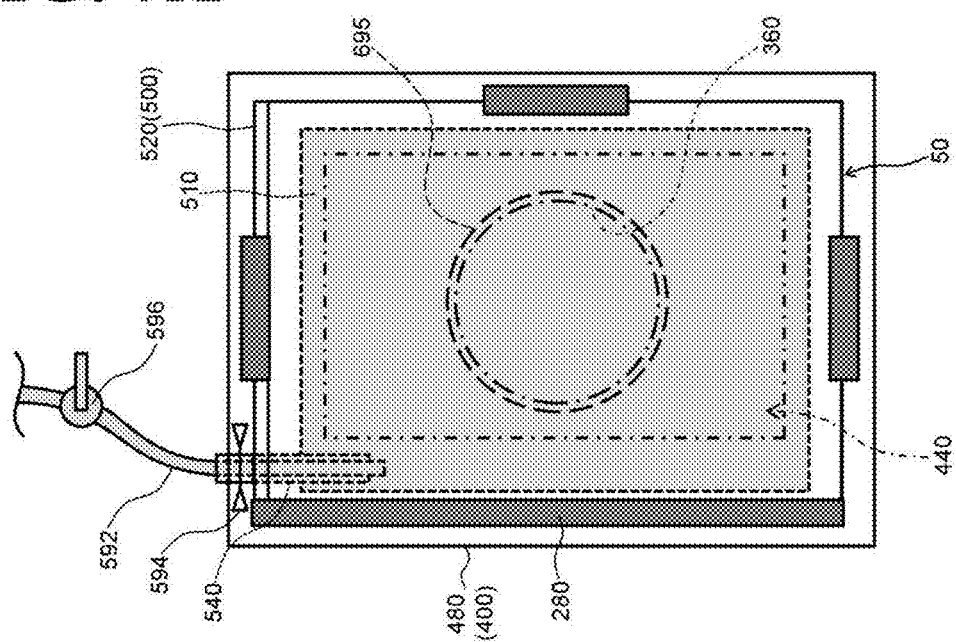
FIG. 7A is a schematic plan view of a part of the acoustic-wave measuring device according to the second embodiment of the present invention.
Figure 7B:
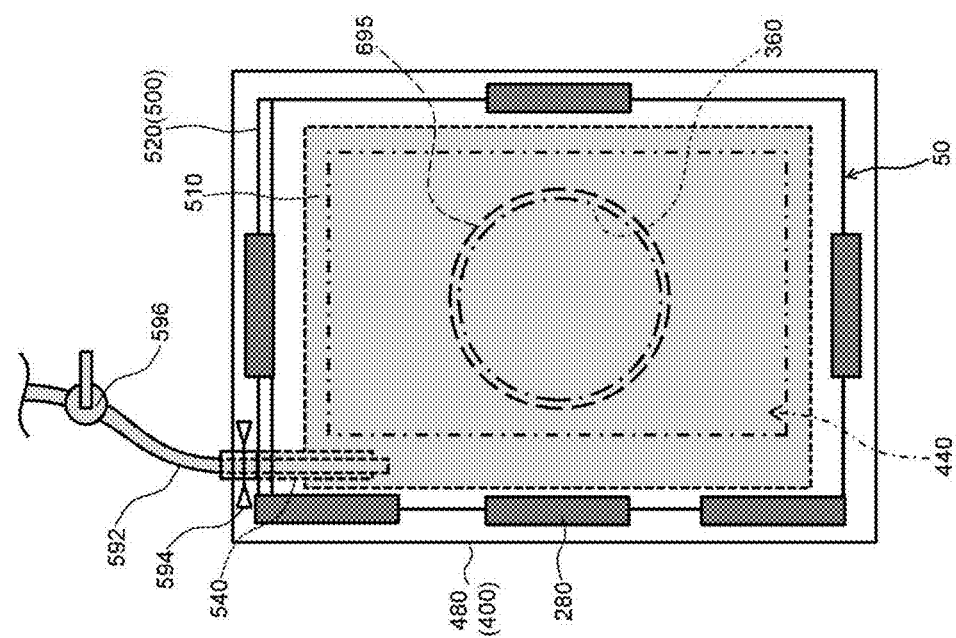
FIG. 7B is a schematic plan view of a part of the acoustic-wave measuring device according to the second embodiment of the present invention.

An acoustic-wave measuring device 10 of the present embodiment will be described with reference to FIGS. 6 to 7B. FIG. 6 is a schematic enlarged view of a part of the acoustic-wave measuring device according to the present embodiment. FIGS. 7A and 7B are schematic plan views of a part of the acoustic-wave measuring device according to the present embodiment.

In the present embodiment, the recessed portion 440 of the placement unit 400 narrows vertically downward, as shown in FIG. 6, for example. In other words, the placement unit 400 has an inner side face 440s that is inclined relative to the support surface 210 so that the recessed portion 440 narrows vertically downward, for example. Specifically, the inner side face 440s of the lower frame 482 is inclined relative to the support surface 210, and the angle of an upper corner portion of the lower frame 482 is obtuse. This can reduce the burden on the examination subject 100.

The acoustic-wave measuring device 10 in the present embodiment is configured so that the matching-material bag 500 is installable to allow the acoustic matching material 510 in the matching-material bag 500 to cover the entire recessed portion 440 (i.e., to extend outward of the peripheral edge of the recessed portion 440), for example. Specifically, the acoustic matching material 510 in the matching-material bag 500 extends to the upper surface of the frame body 480 on the outer side of the peripheral edge of the recessed portion 440, for example. Each fixing member 280 fixes the matching-material bag 500 at a position spaced apart from the peripheral edge of the recessed portion 440 of the frame body 480 by a gap corresponding to the extending portion of the acoustic matching material 510, on the support table 200, for example. With this configuration, even if an end portion of the matching-material bag 500 rises, this end portion can be separated from the imaging region and restrained from affecting imaging.

The placement unit 400 of the present embodiment also has an overflow suppressor 490 that suppresses an overflow of the matching liquid 410 from within the recessed portion 440 to the outside, for example. Specifically, the overflow suppressor 490 is configured as a groove recessed vertically downward from the upper surface of the frame body 480, for example. It is preferable that the overflow suppressor 490 as a groove is located outward of the outer edge of the recessed portion 440 in a plan view and hidden below the matching-material bag 500, for example. It is also preferable that the overflow suppressor 490 as a groove surrounds the recessed portion 440 in a plan view, for example. This configuration can keep the examination site 110 from coming into contact with the overflowing matching liquid 410.

The frame body 480 of the present embodiment has a clamping portion 483 that clamps the holder mesh 460 between this holder 483 and the lower frame 482. The clamping portion 483 is located below the lower frame 482 and fixed to the lower frame 482 while clamping the holder mesh 460 therebetween, for example. The clamping portion 483 is fastened to the lower frame 482 by a bolt (not shown), for example. The lower frame 482 and the clamping portion 483 enable the holder mesh 460 to be firmly locked to the support table 200.

As shown in FIGS. 7A and 7B, the acoustic-wave measuring device 10 of the present embodiment also includes a fluid tube 592, a leakage suppressor 594, and an opener-closer 596, for example.

The fluid tube 592 is configured so that the acoustic matching material 510 can flow therethrough between the matching-material bag 500 and the outside in a state where the matching-material bag 500 is installed, for example. The fluid tube 592 is inserted in the inlet 540 of the matching-material bag 500, for example.

The leakage suppressor 594 is configured to suppress leakage of the acoustic matching material 510 through a gap between the inner circumferential face of the inlet 540 and the outer circumferential face of the fluid tube 592, for example. The leakage suppressor 594 is configured as a fastener that fastens the inlet 540 to the fluid tube 592, for example.

The opener-closer 596 is configured to be capable of opening and closing the fluid tube 592, for example. The amount of acoustic matching material 510 in the matching-material bag 500 can be adjusted by opening and closing the opener-closer 596.

The fluid tube 592, the leakage suppressor 594, and the opener-closer 596 can be considered as not only members constituting the acoustic-wave measuring device 10 but also members used together with the aforementioned matching-material bag 500, as shown in FIGS. 7A and 7B. Accordingly, it may also be considered that the matching-material bag 500, the fluid tube 592, the leakage suppressor 594, and the opener-closer 596 constitute a "matching-material bag set 50".

Also, it is preferable in the present embodiment that the fixing members 280 firmly fix the matching-material bag 500.

Specifically, it is preferable that the fixing members 280 can fix the matching-material bag 500 to the support table 200 over the entirety of one side of the matching-material bag 500 as shown in FIG. 7A, for example.

Alternatively, it is preferable that a plurality of fixing members 280 are provided to fix the matching-material bag 500 to the support table 200 at a plurality of portions on one side of the matching-material bag 500 as shown in FIG. 7B, for example.

(3) Matching-Material Bag

Figure 8A:
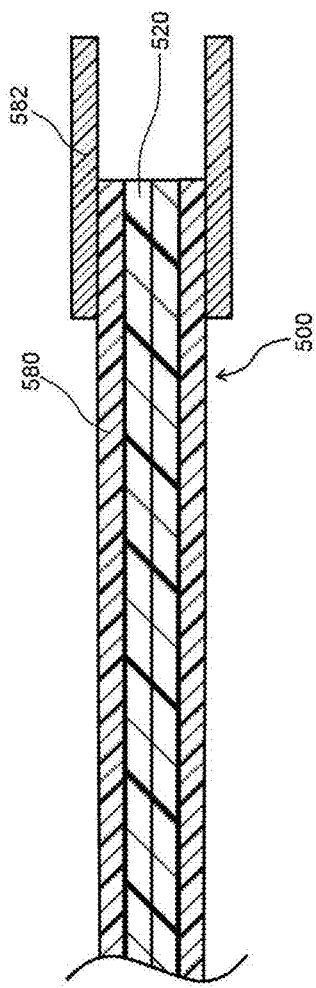
FIG. 8A is a schematic cross-sectional view of a matching-material bag.

The matching-material bag 500 according to the present embodiment will be described with reference to FIG. 8A. FIG. 8A is a schematic cross-sectional view of the matching-material bag.

In the present embodiment, the matching-material bag 500 before use has protective films 580, as shown in FIG. 8A, for example. The protective films 580 cover the bag body 520, are removable from the bag body 520, and protect the bag body 520, for example. It is preferable that the protective films 580 are provided on both the front and back sides of the bag body 520, for example. This configuration can stably protect the bag body 520 before use.

Each protective film 580 also has a holding tab 582 that is held when the protective film 580 is peeled off, for example. The holding tab 582 extends outward from the peripheral edge of the protective film 580, for example. The holding tab 582 may be integrated with the body of the protective film 580 and made of the same material, or may be made of a material different from the body of the protective film 580, for example. This configuration enables the protective film 580 to be easily peeled off.

(4) Acoustic Wave Measurement Method

Figure 8B:
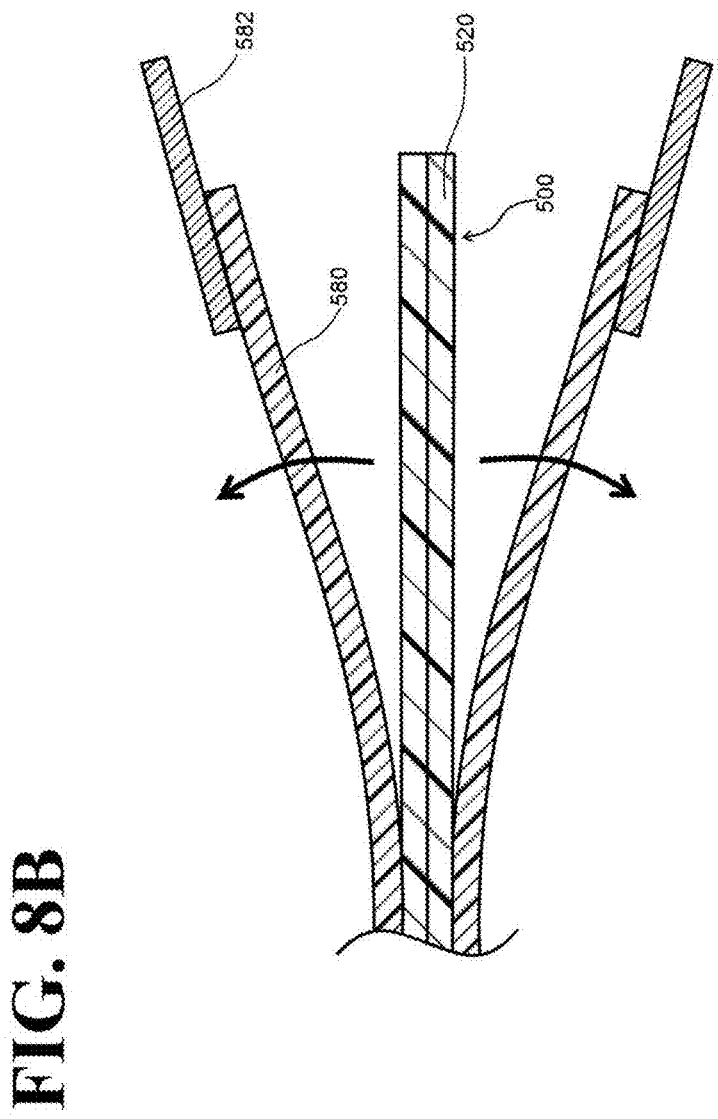
FIG. 8B is a schematic cross-sectional view of the matching-material bag when protective films are peeled off.
Figure 9:
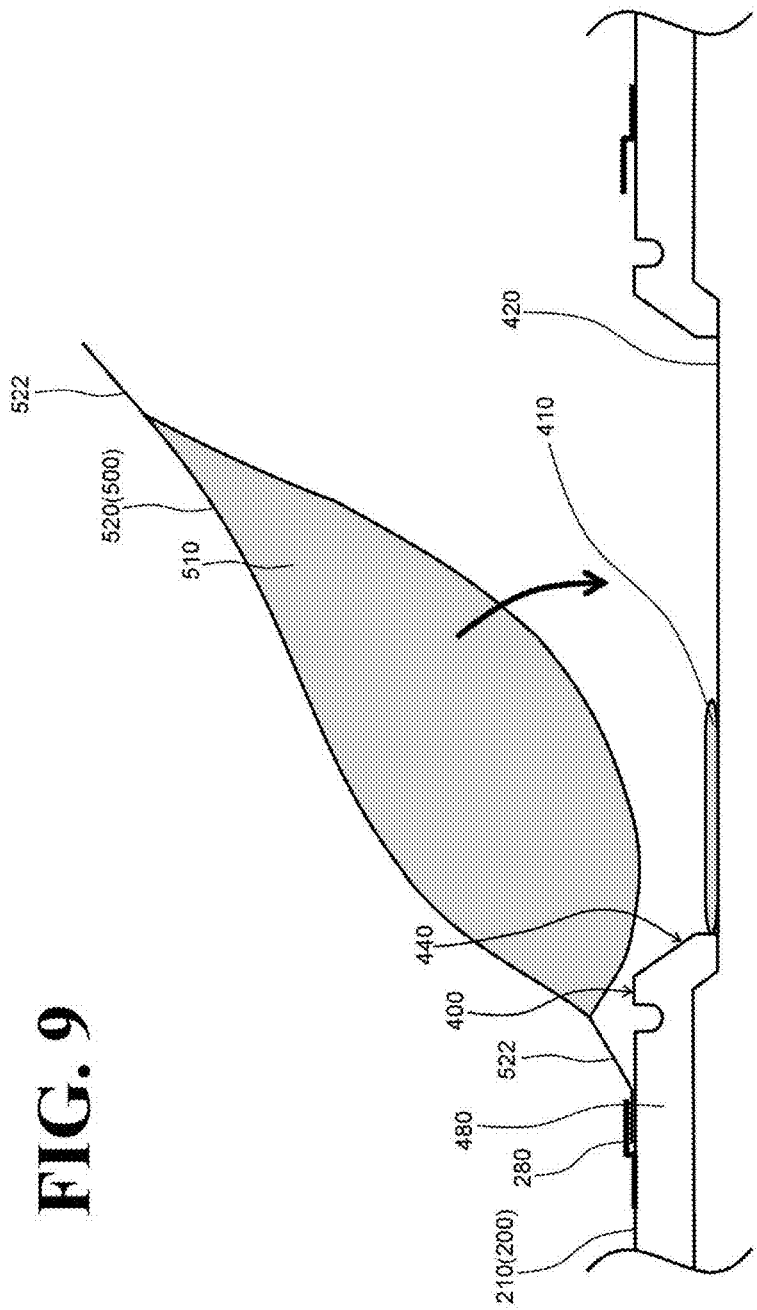
FIG. 9 is a schematic diagram showing the matching-material bag when being placed in a recessed portion of a placement unit.

An acoustic wave measurement method according to the present embodiment will be described with reference to FIGS. 8B and 9. FIG. 8B is a schematic cross-sectional view of the matching-material bag when the protective films are peeled off. FIG. 9 is a schematic diagram showing the matching-material bag when being placed in the recessed portion of the placement unit.

S100: Preparation Step

After the acoustic-wave measuring device 10 is ready, the matching-material bag 500 is prepared. Specifically, the protective films 580 are peeled off from the bag body 520 by pulling the protective films 580 while holding the holding tab 582, as shown in FIG. 8B.

Next, the matching-material bag 500 is fixed to the support table 200 using the fixing members 280, as shown in FIG. 7A, and the matching-material bag 500 is placed in the recessed portion 440 of the placement unit 400 while being pulled so that the matching-material bag 500 is not wrinkled. After the matching-material bag 500 has been placed, the fluid tube 592 is inserted into the inlet 540 of the matching-material bag 500, and the inlet 540 is fastened to (the outer circumferential face of) the fluid tube 592 by the leakage suppressor 594. Note that the matching-material bag 500 may alternatively be placed in the recessed portion 440 of the placement unit 400 after the fluid tube 592 has been inserted and fixed to the inlet 540 of the matching-material bag 500.

Next, the opener-closer 596 is opened to inject the acoustic matching material 510 into the storage space in the matching-material bag 500 via the inlet 540. Here, the lower surface of the bag body 520 is taut and not wrinkled due to the injection of the acoustic matching material 510, but the upper surface of the bag body 520 is wrinkled since it is not taut. Therefore, the matching-material bag 500 is filled with the acoustic matching material 510 so as to eliminate the wrinkles on the upper surface of the bag body 520. In this state, the opener-closer 596 is closed.

Next, with one side of the matching-material bag 500 fixed by the fixing member 280, the matching-material bag 500 is folded back toward the opposite side of the recessed portion 440 of the placement unit 400 with the above-mentioned one side of the matching-material bag 500 interposed therebetween. After the matching-material bag 500 has been folded back, a small amount of matching liquid 410 is injected into the recessed portion 440 of the placement unit 400. Here, it is preferable to inject the matching liquid 410 into the recessed portion 440 so that the one side of the matching-material bag 500 that is the reference for the fold-back is parallel with the matching liquid 410.

Next, as shown in FIG. 9, the opposite side to the one side of the matching-material bag 500 that is the reference for the fold-back is held to pull and raise the matching-material bag 500. The matching-material bag 500 is gradually lowered from an end of the recessed portion 440 on the side on which the matching-material bag 500 has been folded back, and is placed in the recessed portion 440 so that no bubble enters between the matching-material bag 500 and the separation film 420.

Here, if the bag body 520 of the matching-material bag 500 is wrinkled, the fixation margin 522 of the bag body 520 is pulled to eliminate the wrinkles from the upper and lower surfaces of the bag body 520.

After the bag body 520 is ready, the fixation margin 522 of the bag body 520 is loosened on another side opposite to the side of the matching-material bag 500 that is the reference for the fold-back, and is fixed to the support table 200 using the fixing members 280. Displacement of the matching-material bag 500 that occurs when the examination site 110 is placed on the matching-material bag 500 can be absorbed by loosening the fixation margin 522 of the bag body 520.

S200: Placement Step

Next, the examination site 110 is placed on the matching-material bag 500.

Here, the amount of acoustic matching material 510 in the matching-material bag 500 is adjusted by opening and closing the opener-closer 596 while checking the image acquired by the imaging unit 690. The examination site 110 can thus be brought close to the receiving unit 300. That is, the examination site 110 can be arranged within the field of view (FOV) of the receiving unit 300, thus enabling to obtain a high-quality image. Further, movement (body movement) of the examination site 110 can be suppressed by causing the examination site 110 to sink into the matching-material bag 500. Furthermore, a rise of the end portions of the matching-material bag 500 can be suppressed.

Steps after the placement step S200, including the measurement step S300, are the same as the above-described first embodiment.

(5) Effects Achieved by the Present Embodiment (a) The recessed portion 440 of the placement unit 400 in the present embodiment narrows vertically downward. This allows the upper corner portions of the recessed portion 440 to be inclined relative to the support surface 210. This configuration can alleviate the pain felt by the examination subject 100 even if the examination site 110 comes into contact with the upper corner portions of the recessed portion 440 due to the device state. As a result, the burden on the examination subject 100 can be reduced.

(b) The acoustic-wave measuring device 10 in the present embodiment is configured so that the matching-material bag 500 is installable to allow the acoustic matching material 510 in the matching-material bag 500 to cover the entire recessed portion 440. Even if the examination site 110 greatly sinks into the matching-material bag 500 and the end portions of the matching-material bag 500 rise, these end portions can be separated from the imaging region and kept from affecting imaging. That is, the acoustic matching material 510 in the matching-material bag 500 can be maintained in intimate contact with the matching liquid 410 to the ends of the recessed portion 440. As a result, it is possible to match the acoustic impedance with the examination subject 100 over a wide area and stably measure acoustic waves.

(c) The placement unit 400 in the present embodiment has an overflow suppressor 490 that suppresses an overflow of the matching liquid 410 from within the recessed portion 440 to the outside. Even if the matching-material bag 500 is tightly placed in the recessed portion 440 and the matching liquid 410 is about to overflow from within the recessed portion 440 to the outside, it is possible to keep the overflowing matching liquid 410 within the overflow suppressor 490 and suppress a further spread of the matching liquid 410. This can keep the examination site 110 from coming into contact with the overflowing matching liquid 410.

(d) The inlet 540 in the present embodiment brings the outer edge of the bag body 520 into communication with the inside and is configured so that the acoustic matching material 510 can be injected into the storage space in the matching-material bag 500. This enables the acoustic matching material 510 to be stably injected via the inlet 540.

The fluid tube 592 is configured so that the acoustic matching material 510 can flow between the matching-material bag 500 and the outside space in a state where the matching-material bag 500 is installed. The opener-closer 596 can open and close the fluid tube 592. The amount of acoustic matching material 510 in the matching-material bag 500 can be adjusted by opening and closing the opener-closer 596.

With the above configuration, even if, for example, the examination site 110 is placed on the matching-material bag 500 and then the end portions of the matching-material bag 500 rise, the acoustic matching material 510 can flow out from the matching-material bag 500, and the amount of acoustic matching material 510 in the matching-material bag 500 can be reduced. As a result, even if the end portions of the matching-material bag 500 rise, these end portions can be separated from the imaging region and kept from affecting imaging.

(e) The leakage suppressor 594 in the present embodiment is configured to suppress leakage of the acoustic matching material 510 from between the inner circumferential face of the inlet 540 and the outer circumferential face of the fluid tube 592. This enables the acoustic matching material 510 to stably flow in and out via the inlet 540 while suppressing leakage of the acoustic matching material 510. Further, the examination site 110 can be kept from being wetted by the acoustic matching material 510.

(f) The matching-material bag 500 in the present embodiment has the protective films 580. The protective films 580 cover the bag body 520, are removable from the bag body 520, and protect the bag body 520. This can stably protect the bag body 520 before use. For example, contamination and damage to the surfaces of the matching-material bag 500 can be suppressed. As a result, the cleanliness and rigidity (shape stability) of the matching-material bag 500 can be stably ensured.

(6) Variations of Second Embodiment

Variation 2-1

Figure 10:
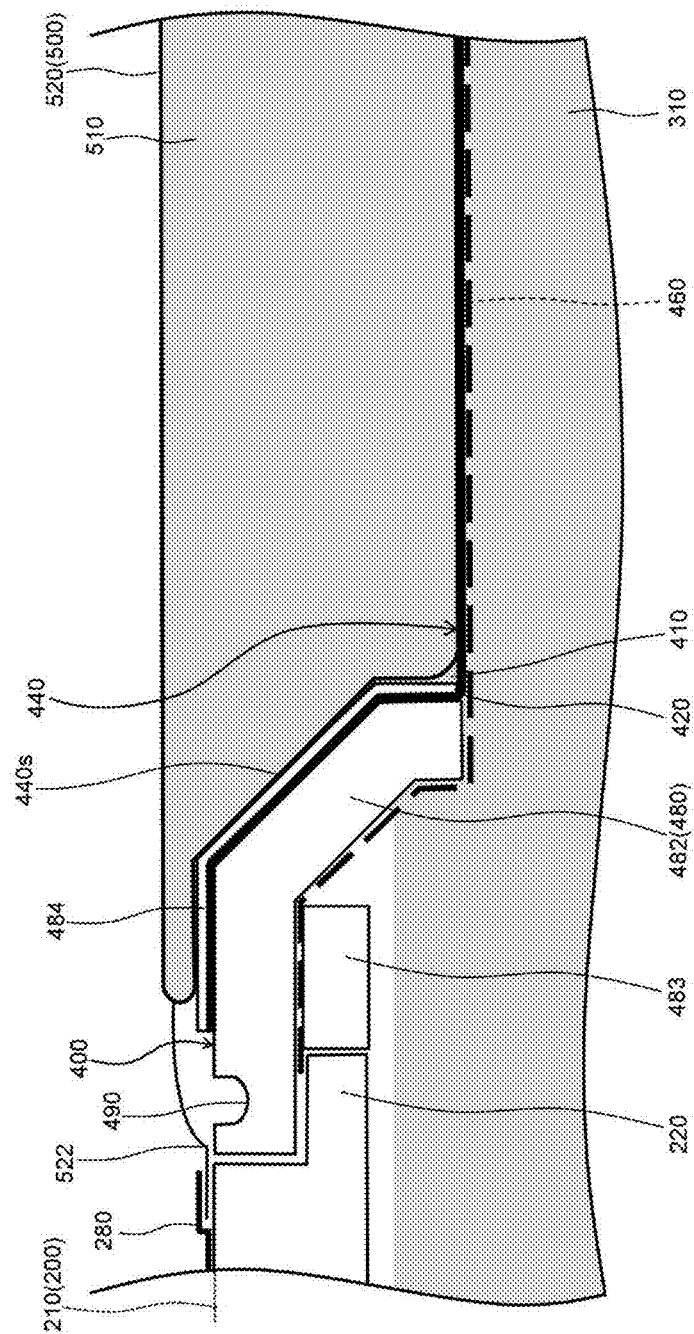
FIG. 10 is a schematic enlarged view of a part of an acoustic-wave measuring device according to a variation 2-1 of the second embodiment of the present invention.

An acoustic-wave measuring device 10 of a variation 2-1 of the present embodiment will be described with reference to FIG. 10. FIG. 10 is a schematic enlarged view of a part of the acoustic-wave measuring device according to the variation 2-1 of the present embodiment.

The variation 2-1 is different from the above embodiment in the configuration of the frame body 480.

As shown in FIG. 10, the recessed portion 440 of the placement unit 400 in this variation narrows vertically downward, similarly to the above embodiment, for example.

The upper frame 484 of the frame body 480 in this variation has a shape similar to the shape of the inner side face 440s that is inclined relative to the support surface 210 from the upper end to the lower end of the recessed portion 440, for example. The upper frame 484 holds the separation film 420 between the upper frame 484 and the lower frame 482, for example.

According to this variation, the separation film 420 can be held in a wider range between the lower frame 482 and the upper frame 484. This enables the frame body 480 to stably hold the separation film 420. Also, the three-dimensional shape of the separation film 420 can be easily formed by using the frame body 480 that can be repeatedly used and holding the separation film 420 with use of the lower frame 482 and the upper frame 484. That is, the step of manually shaping the separation film 420 can be omitted.

Variation 2-2

Figure 11:
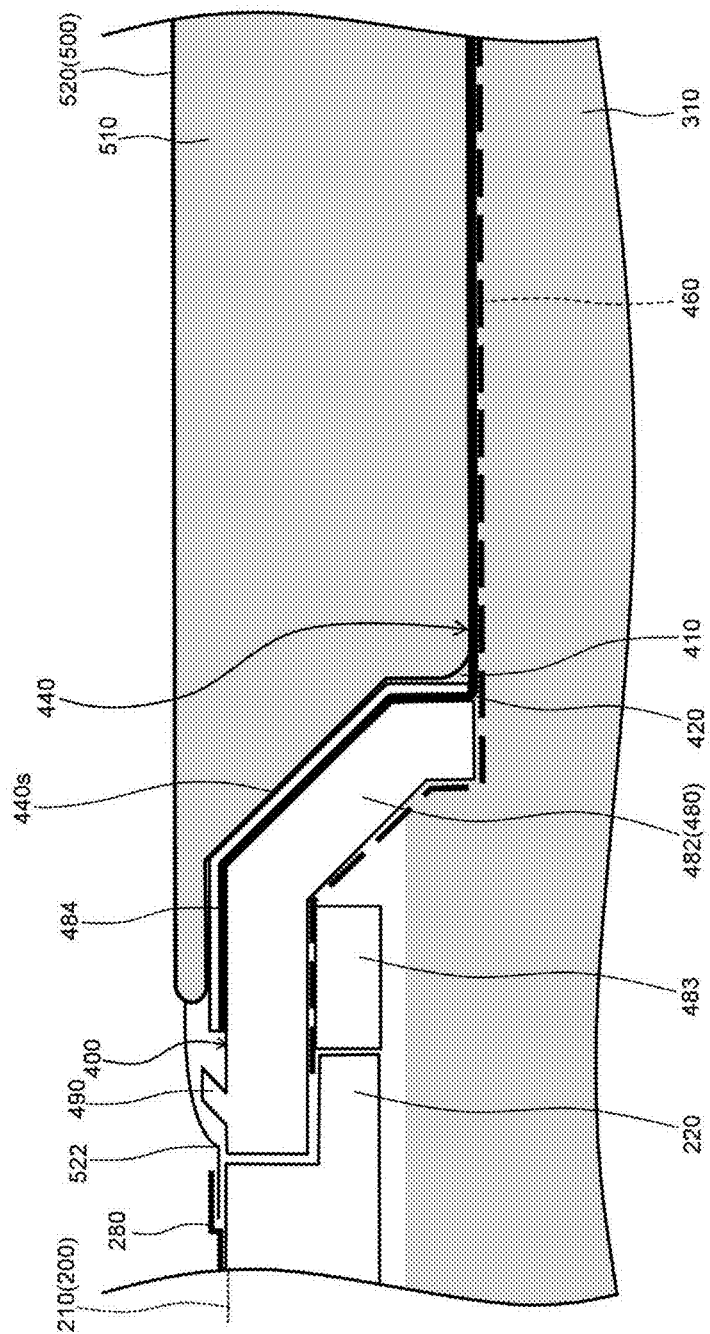
FIG. 11 is a schematic enlarged view of a part of an acoustic-wave measuring device according to a variation 2-2 of the second embodiment of the present invention.

An acoustic-wave measuring device 10 of a variation 2-2 of the present embodiment will be described with reference to FIG. 11. FIG. 11 is a schematic enlarged view of a part of the acoustic-wave measuring device according to the variation 2-2 of the present embodiment.

The variation 2-2 is different from the above embodiment in the configuration of the overflow suppressor 490.

As shown in FIG. 11, the overflow suppressor 490 in this variation is configured as a bank (embankment, mound) that restricts the spread of the matching liquid 410 from the recessed portion 440 to the outside, for example. Specifically, the overflow suppressor 490 as a bank protrudes obliquely upward toward the center of the recessed portion 440 from the upper surface of the frame body 480, for example. Also, the overflow suppressor 490 surrounds the recessed portion 440 in a plan view, for example.

This variation can also keep the examination site 110 from coming into contact with the overflowing matching liquid 410.

Variation 2-3

Figure 12:
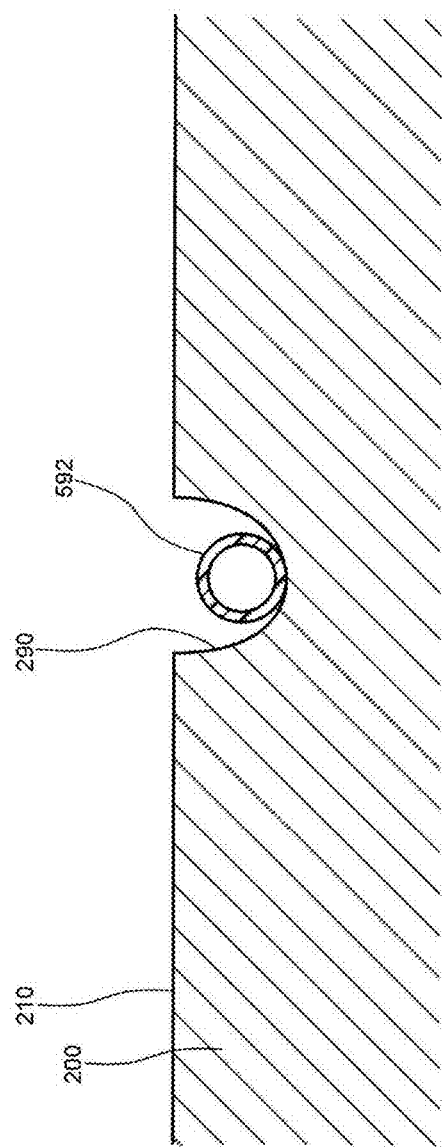
FIG. 12 is a schematic cross-sectional view of a part of an acoustic-wave measuring device according to a variation 2-3 of the second embodiment of the present invention.

An acoustic-wave measuring device 10 of a variation 2-3 of the present embodiment will be described with reference to FIG. 12. FIG. 12 is a schematic cross-sectional view of a part of the acoustic-wave measuring device according to the variation 2-3 of the present embodiment.

The variation 2-3 is different from the above embodiment in the configuration of the support table 200.

As shown in FIG. 12, the support table 200 in this variation is configured so that the fluid tube 592 can be arranged vertically below the support surface 210, for example. Specifically, the support table 200 has a groove 290 that is recessed vertically downward from support surface 210 and accommodates the fluid tube 592, for example.

According to this variation, the fluid tube 592 can be restrained from protruding upward of the support surface 210 even in a state where the matching-material bag 500 is placed in the recessed portion 440. This can keep the examination site 110 from riding over the fluid tube 592 and blocking the fluid tube 592. As a result, the acoustic matching material 510 can stably flow between the matching-material bag 500 and the outside space.

Variation 2-4

Figure 13:
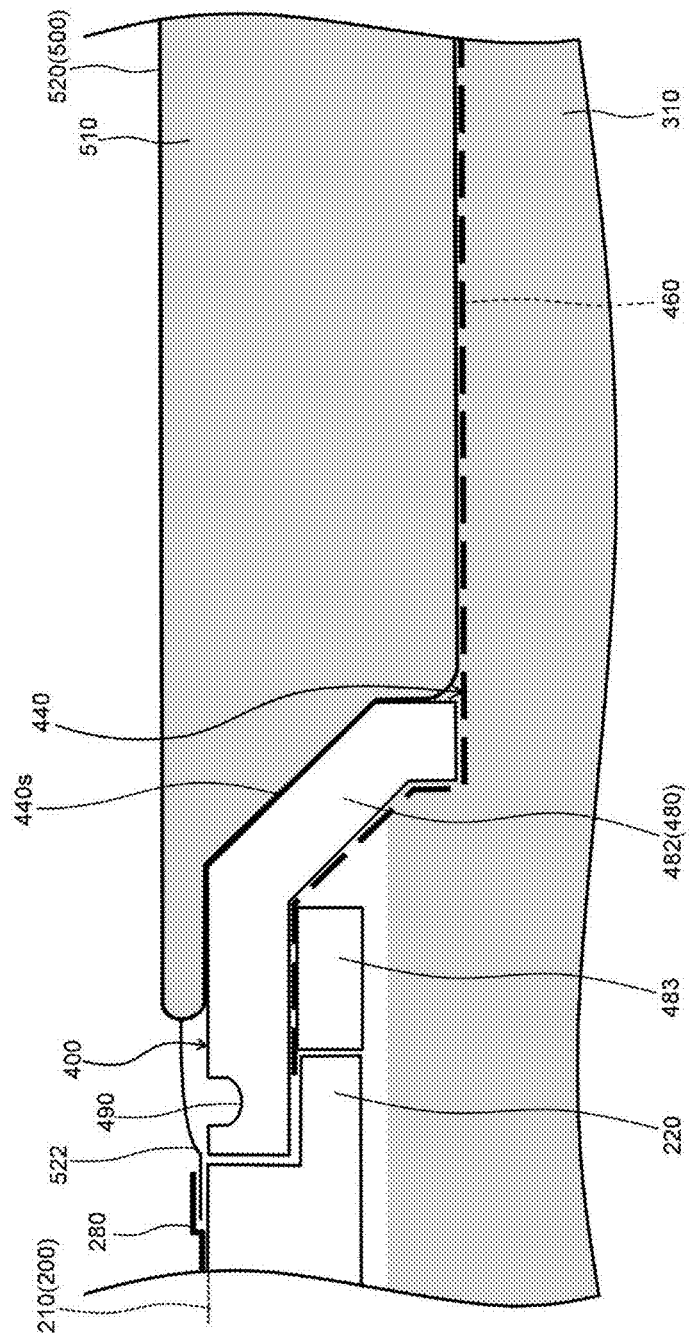
FIG. 13 is a schematic cross-sectional view of a part of an acoustic-wave measuring device according to a variation 2-4 of the second embodiment of the present invention.

An acoustic-wave measuring device 10 of a variation 2-4 of the present embodiment will be described with reference to FIG. 13. FIG. 13 is a schematic cross-sectional view of a part of the acoustic-wave measuring device according to the variation 2-4 of the present embodiment.

The variation 2-4 is different from the above embodiment in that the separation film 420 is not provided.

In this variation, the opening portion 220 of the support table 200 narrows vertically downward, as shown in FIG. 13. The acoustic-wave measuring device 10 is configured so that the matching-material bag 500 or a matching gel is installable directly on the holder mesh 460 so as to cover the entire opening portion 220 without installing the separation film 420. Accordingly, the upper frame 484 for pressing the separation film 420, as well as the separation film 420, is unnecessary.

According to this variation, the matching-material bag 500 or the matching gel can also serve as the separation film 420. That is, it is possible, without providing the separation film 420, to prevent the acoustic matching material 310 from penetrating into the examination site 110 side and keep the acoustic matching material 310 from overflowing outward of the opening portion 220. Further, degradation of image quality due to the separation film 420 can be suppressed.

In this variation, it is preferable to use the matching-material bag 500. In the case of using a matching gel, there is a concern that the matching gel enters holes in the holder mesh 460, whereas the matching-material bag 500 has no such concern. It is, therefore, preferable to use the matching-material bag 500.

OTHER EMBODIMENTS

The embodiments of the present invention have been described above in detail.

However, the present invention is not limited to the above-described embodiments, and various changes can be made without departing from the gist thereof.

The above embodiments have described the case where the acoustic-wave measuring device 10 is configured as a PAT device, but the acoustic-wave measuring device 10 may alternatively be configured as any device other than a PAT device as long as acoustic waves can be measured. For example, the acoustic-wave measuring device 10 may alternatively be configured as an ultrasonic echo device that applies acoustic waves (ultrasonic waves) to the predetermined examination site 110 of the examination subject 100 and receives acoustic waves (reflected waves) reflected or scattered from the area to which the acoustic waves have been applied.

The above embodiments have described the case where the acoustic-wave measuring device 10 is configured so that the separation film 420 and the matching-material bag 500 are installable in this order between the acoustic matching material 310 contained in the container 320 and the examination site 110, but this need not be the case. The acoustic-wave measuring device 10 may alternatively be configured so that the separation film 420 and a matching gel are installable in this order between the acoustic matching material 310 contained in the container 320 and the examination site 110. The matching gel has limited flowability and an acoustic control effect, for example. Note that "limited flowability" refers to maintaining the bound state while having the ability to follow the examination site 110, for example. "Having an acoustic control effect" refers to having an acoustic impedance that matches the examination subject 100, for example. Specific examples of the matching gel include a nanocomposite gel. In this case, the matching liquid 410 need not be provided in the recessed portion 440 of the placement unit 400, as will be described later. The same effects as the above embodiments can also be obtained by using this type of matching gel.

The acoustic-wave measuring device 10 may also be configured so that the separation film 420 and a matching block that is a combination of the matching-material bag 500 and the matching gel are installable in this order between the acoustic matching material 310 contained in the container 320 and the examination site 110.

The above embodiments have described the case where the element holder 360 has a hemispherical shape, but the element holder 360 may alternatively have any shape other than the hemispherical shape. The element holder 360 may alternatively have a flat plate shape, for example.

The above embodiments have described the case where the light outlet 660 is provided at the bottom portion of the element holder 360, but the light outlet 660 may alternatively be provided at any position other than the bottom portion of the element holder 360 as long as the light transmitted from the light source 620 can be emitted toward the examination site 110. The light outlet 660 may alternatively be provided at a side portion of the container 320, for example.

The above embodiments have described the case where the scanning mechanism 380 relatively scan the receiving elements 340 with respect to the examination subject 100 placed on the support table 200, but this need not be the case as long as the examination subject 100 and the receiving elements 340 can be moved relative to each other. The scanning mechanism 380 may alternatively be configured to move the examination subject 100 (i.e., support table 200) relative to fixed receiving element 340 for scanning, for example. Alternatively, the scanning mechanism 380 may be configured to move both the receiving elements 340 and the examination subject 100 relative to each other for scanning.

The above embodiments have described the case where the scanning mechanism 380 causes the receiving unit 300 as an integral unit having the container 320 and the receiving elements 340 to scan, but this need not be the case. The scanning mechanism 380 may alternatively be configured to cause the element holder 360 having the plurality of receiving elements 340 to scan within the fixed container 320, for example.

The above embodiments have described the case where the matching liquid 410 is provided between the separation film 420 and the matching-material bag 500. However, if a matching gel such as a nanocomposite gel with high moisture content is used instead of the matching-material bag 500, the moisture on the surface of the matching gel itself makes it possible to obtain sufficient signals without separately preparing the matching liquid 410. Accordingly, providing the recessed portion 440 and using the matching liquid 410 is not necessarily essential in the case of using this type of nanocomposite gel or the like.

The above embodiments have described the case where the placement unit 400 has a separation film 420 that is recessed on its own, but this need not be the case as long as the separation film 420 at least constitutes the bottom portion of the recessed portion 440 of the placement unit 400. For example, the placement unit 400 may have a frame body 480 that is recessed vertically downward, and a flat separation film 420 provided along the lower surface of the frame body 480. According to this case, the recessed portion 440 of the placement unit 400 can be easily formed even if the separation film 420 is thin.

The above embodiments have described the case where the inlet 540 of the matching-material bag 500 is constituted by a film, but the inlet 540 may alternatively be constituted by a spout or a connector. However, the inlet 540 is preferably constituted by a film as in the above embodiments since a person to be examined as the examination subject 100 does not feel pain.

The above embodiments have described the case where the fixing members 280 for fixing the matching-material bag 500 are configured as binders, but this need not be the case. The fixing members 280 may alternatively be members separated from the support table 200. Specifically, the fixing members 280 may be adhesive tape, for example. Alternatively, the fixing members 280 may be configured as magnets holding the matching-material bag 500 by magnetic force, for example.

The above embodiments have described the case where the opener-closer 596 is configured to open and close the fluid tube 592, but the opener-closer 596 may alternatively be configured to open and close the inlet 540.

Preferred Modes of the Present Invention

Preferred modes of the present invention will be described below.

(Supplementary Note 1)

An acoustic-wave measuring device including:

a support table having a support surface configured to support an examination subject, and an opening portion provided in the support surface in order to measure a predetermined examination site of the examination subject;

a container located vertically below the support surface and capable of containing an acoustic matching material in a liquid or gel form; and a receiving element located vertically below the support surface and configured to receive an acoustic wave generated from the examination site, wherein a matching-material bag containing an acoustic matching material in a liquid or gel form or a matching gel having limited flowability and an acoustic control effect, and a placement unit for placement of the matching-material bag or the matching gel thereon are installable between the acoustic matching material contained in the container and the examination site.

(Supplementary Note 2)

The acoustic-wave measuring device according to supplementary note 1, wherein a separation film that does not allow the acoustic matching material to permeate is installable as the placement unit, and the separation film and the matching-material bag or the matching gel are installable in stated order between the acoustic matching material contained in the container and the examination site.

(Supplementary Note 3)

The acoustic-wave measuring device according to supplementary note 2, wherein the placement unit has a recessed portion that is recessed vertically downward of the support surface, and the separation film constitutes at least a bottom portion of the recessed portion.

(Supplementary Note 4)

The acoustic-wave measuring device according to supplementary note 3, wherein the recessed portion narrows vertically downward.

(Supplementary Note 5)

The acoustic-wave measuring device according to supplementary note 3 or 4, wherein the matching-material bag or the matching gel is installable to allow the acoustic matching material in the matching-material bag or the matching gel to cover an entirety of the recessed portion.

(Supplementary Note 6)

The acoustic-wave measuring device according to any one of supplementary notes 3 to 5, wherein the placement unit is capable of containing a matching liquid in the recessed portion.

(Supplementary Note 7)

The acoustic-wave measuring device according to supplementary note 6, wherein the placement unit has an overflow suppressor configured to suppress overflow of the matching liquid out from within the recessed portion.

(Supplementary Note 8)

The acoustic-wave measuring device according to any one of supplementary notes 1 to 7, wherein a holder mesh configured to hold the matching-material bag or the matching gel and the examination site is installable as the placement unit, the holder mesh and the matching-material bag or the matching gel are installable in stated order between the acoustic matching material contained in the container and the examination site, and the holder mesh and an upper surface of the acoustic matching material in the container are capable of being brought close to each other to allow the acoustic matching material in the container to block holes in the holder mesh.

(Supplementary Note 9)

The acoustic-wave measuring device according to supplementary note 1, wherein the opening portion narrows vertically downward, and the matching-material bag or the matching gel is installable so as to cover an entirety of opening portion.

(Supplementary Note 10)

The acoustic-wave measuring device according to any one of supplementary notes 1 to 9, further including:

a fluid tube through which the acoustic matching material is flowable between the matching-material bag and an outside space in a state where the matching-material bag is installed; and an opener-closer configured to open and close the fluid tube.

(Supplementary Note 11)

The acoustic-wave measuring device according to supplementary note 10, wherein the support table is configured such that the fluid tube is installable vertically below the support surface.

(Supplementary Note 12)

The acoustic-wave measuring device according to any one of supplementary notes 1 to 11, wherein the matching-material bag or the matching gel is fixable to the support table with use of a predetermined fixing member.

(Supplementary Note 13)

The acoustic-wave measuring device according to any one of the supplementary notes 1 to 12, wherein the matching-material bag is installable so that, in a state where the examination subject is placed on the support surface, an upper surface of the matching-material bag is at least partially located at the same height as the support surface, or is located vertically above the support surface.

(Supplementary Note 14)

The acoustic-wave measuring device according to any one of the supplementary notes 1 to 13, wherein the matching-material bag is installable so that, in a state where the examination subject is not placed on the support surface, an upper surface of the matching-material bag is at least partially located at the same height as the support surface or is located vertically above the support surface, (Supplementary Note 15)

A matching-material bag for use in the acoustic-wave measuring device according to any one of the supplementary notes 1 to 14.

(Supplementary Note 16)

A matching gel for use in the acoustic-wave measuring device according to any one of the supplementary notes 1 to 14.

(Supplementary Note 17)

A separation film for use in the acoustic-wave measuring device according to any one of the supplementary notes 2 to 7.

(Supplementary Note 18)

An acoustic wave measurement method including:

preparing an acoustic-wave measuring device including a support table having a support surface and an opening portion provided in the support surface in order to measure a predetermined examination site of an examination subject, a container located vertically below the support surface and containing an acoustic matching material in a liquid or gel form, and a receiving element located vertically below the support surface;

placing the examination subject on the support surface of the support table; and receiving an acoustic wave generated from the examination site, with use of the receiving element, wherein in the preparing of the acoustic-wave measuring device, a matching-material bag containing an acoustic matching material in a liquid or gel form or a matching gel having limited flowability and an acoustic control effect, and a placement unit for placement of the matching-material bag or the matching gel thereon are installed between the acoustic matching material contained in the container and the examination site.

REFERENCE SIGNS LIST

10 Acoustic-wave measuring device
100 Examination subject
110 Examination site
200 Support table
300 Receiving unit
310 Acoustic matching material
320 Container
340 Receiving element
400 Placement unit
410 Acoustic matching material
420 Separation film
500 Matching-material bag
510 Acoustic matching material

The invention claimed is:

1. An acoustic-wave measuring device comprising:
a support table having a support surface configured to support an examination subject, and an opening portion in the support surface to measure a predetermined examination site of the examination subject;
a container vertically below the support surface and configured to contain a first acoustic matching material in liquid or gel form;
a placement unit between the first acoustic matching material contained in the container and the examination site;
a matching-material bag containing a second acoustic matching material in liquid or gel form, the matching-material bag being on the placement unit between the first acoustic matching material in the container and the examination site; and
a receiving element vertically below the support surface and configured to receive an acoustic wave generated from the examination site via the first acoustic matching material, the placement unit, and the matching-material bag, wherein the matching-material bag has a bag body film surrounding a storage space containing the second acoustic matching material, and the bag body film is configured to prevent the examination subject from directly contacting the second acoustic matching material.

2. The acoustic-wave measuring device according to claim 1, wherein the placement unit has a separation film that does not allow the first acoustic matching material to permeate, and the separation film and the matching-material bag are installed in stated order between the first acoustic matching material in the container and the examination site.

3. The acoustic-wave measuring device according to claim 2, wherein the placement unit has a recessed portion that is recessed vertically downward of the support surface, and the separation film constitutes at least a bottom portion of the recessed portion.

4. The acoustic-wave measuring device according to claim 3, wherein the recessed portion narrows vertically downward.

5. The acoustic-wave measuring device according to claim 3, wherein the matching-material bag is configured so that the second acoustic matching material in the matching-material bag covers an entirety of the recessed portion.

6. The acoustic-wave measuring device according to claim 3, wherein the placement unit is configured to contain a third acoustic matching material in liquid in the recessed portion.

7. The acoustic-wave measuring device according to claim 6, wherein the placement unit has an overflow suppressor configured to suppress overflow of the third acoustic matching material out from within the recessed portion.

8. The acoustic-wave measuring device according to claim 1, wherein the placement unit has a holder mesh configured to hold the matching-material bag and the examination site, the holder mesh and the matching-material bag are installed in stated order between the first acoustic matching material in the container and the examination site, and the holder mesh is configured to be in contact with an upper surface of the first acoustic matching material in the container to allow the first acoustic matching material in the container to enter into holes in the holder mesh.

9. The acoustic-wave measuring device according to claim 1, wherein the opening portion narrows vertically downward, and the matching-material bag covers an entirety of the opening portion.

10. The acoustic-wave measuring device according to claim 1, further comprising:

a fluid tube through which the second acoustic matching material is flowable between the matching-material bag and an outside space in a state where the matching-material bag is installed; and an opener-closer configured to open and close the fluid tube.

11. The acoustic-wave measuring device according to claim 10, wherein the support table is configured such that the fluid tube is installable vertically below the support surface.

12. The acoustic-wave measuring device according to claim 1, wherein the matching-material bag is fixable to the support table by a predetermined fixing member.

13. The acoustic-wave measuring device according to claim 3, wherein the matching-material bag has an inlet configured to allow the second acoustic matching material to be injected into the matching-material bag.

14. The acoustic-wave measuring device according to claim 13, wherein the inlet is outside the recessed portion in a state where the matching-material bag is on the separation film.

15. The acoustic-wave measuring device according to claim 12, wherein the matching-material bag has a fixation margin fixable to the support table with the fixing member.

16. An acoustic wave measurement method comprising:

preparing an acoustic-wave measuring device including a support table having a support surface and an opening portion in the support surface to measure a predetermined examination site of an examination subject, a container vertically below the support surface and containing a first acoustic matching material in liquid or gel form, and a receiving element vertically below the support surface;

placing the examination subject on the support surface of the support table; and receiving an acoustic wave generated from the examination site with the receiving element, wherein in the preparing of the acoustic-wave measuring device, a placement unit and a matching-material bag containing a second acoustic matching material in liquid or gel form, the matching-material bag being on the placement unit, are between the first acoustic matching material in the container and the examination site, the matching-material bag has a bag body film surrounding a storage space containing the second acoustic matching material, the bag body film is configured to prevent the examination subject from directly contacting the second acoustic matching material, and in the receiving the acoustic wave, the acoustic wave generated from the examination site is received by the receiving element, via the first acoustic matching material, the placement unit, and the matching-material bag.

* * * * *